(12) United States Patent
Williams

(10) Patent No.: US 6,413,251 B1
(45) Date of Patent: Jul. 2, 2002

(54) METHOD AND SYSTEM FOR CONTROLLING A DIGITAL MIRCOMIRROR DEVICE FOR LASER REFRACTIVE EYE SURGERY

(75) Inventor: Roy E. Williams, Collierville, TN (US)

(73) Assignee: Memphis Eye & Cataract Associates Ambulatory Surgery Center, Memphis, TN (US)

( * ) Notice: Subject to any disclaimer, the term of this patent is extended or adjusted under 35 U.S.C. 154(b) by 0 days.

(21) Appl. No.: 09/567,155

(22) Filed: May 9, 2000

Related U.S. Application Data

(63) Continuation-in-part of application No. 09/524,312, filed on Mar. 13, 2000.

(51) Int. Cl.$^7$ ............................................... A61B 18/18
(52) U.S. Cl. ................................ 606/5; 606/4; 606/17; 606/18; 356/24; 128/898
(58) Field of Search ........................... 606/4–6, 10–13, 606/17, 18; 356/2, 4.09, 24, 27; 128/898

(56) References Cited

U.S. PATENT DOCUMENTS

| | | | |
|---|---|---|---|
| 5,624,437 A | * 4/1997 | Freeman et al. | 606/12 |
| 5,777,719 A | 7/1998 | Williams et al. | 351/212 |
| 5,782,822 A | * 7/1998 | Telrair et al. | 606/5 |
| 6,099,522 A | * 8/2000 | Knopp et al. | 606/10 |
| 6,129,722 A | * 10/2000 | Ruiz | 606/5 |

OTHER PUBLICATIONS

Article on Photorefractive keratectomy: a technique for laser refractive surgery by Munnerlyn, koons, and Marshall in Cataract Refract Surg, vol. 14, Jan. 1988,pp. 46–52.

Abstract for "Changes in Corneal Aberration Structure After Photorefractive Keratectomy" by Martinez et al., 1 page.
Article entitled "Effect of Pupillary Dilation on Corneal Optical Aberrations after Photorefractive Keratectomy" by Martinez et al. In ARCH Opthalmol/vol. 116, Aug. 1998, pp. 1053–1062.
Article entitled "Anatomically accurate, finite model eye for optical modelling", by Liou et al. for the J. Opt. Soc. Am, A/vol. 14, No. 8/Aug. 1997, pp. 1684–1695.
Article entitled "Custom photorefractive keratectomy ablations for the correction of spherical and cylindrical refractive error and higher–order aberration" by Schwiegerling et al., in J. Opt. Soc. Am, A/vol. 15, No. 9, Sep. 1998, pp. 2572–2579.
Article entitled "Objective measurement of wave aberrations of the human eye with the use of the Hartmann–Shack wave–front sensor" by Liang et al., vol. 11, No. 7/Jul. 1994,J. Opt. Soc. Am A, pp. 1949–1957.s.
Article entitled, "Refractive Surgery– Customized ablations: the future is close", by Arons, in SLACK Inc, newspaper, Feb. 15, 2000.

(List continued on next page.)

Primary Examiner—Linda C. M. Dvorak
Assistant Examiner—Ahmed Farah
(74) Attorney, Agent, or Firm—David P Gordon; David S Jacobson; Thomas A Gallagher

(57) ABSTRACT

A laser eye surgery system includes a laser for producing a laser beam capable of making refractive corrections, an optical system for shaping and conditioning the laser beam, a digital micromirror device (DMD) for reflecting the shaped and conditioned beam toward the eye, and a computer system for controlling the mirrors of the DMD. The computer system generates one-bit resolution images corresponding to ablation layers defining a correction for the eye. The images are then transferred to the DMD for appropriate reflection of the laser beam toward the eye such that the shape of the cornea of the eye is corrected.

9 Claims, 26 Drawing Sheets

OTHER PUBLICATIONS

Webpage downloaded Feb. 14, 2000 for "Wavefront measurements may replace eye charts", by Deena Beasley (Feb. 13, 2000), 3 pages.

Specifications page on Wavescope, Wavefront Sensor System WFS–01, 1997.

Article entitled Optical profilometry of poly(methylmethacrylate) surfaces after reshaping with a photorefractive keratectomy (SPRK) system, by Manns et al. in Applied Optics, vol. 35, No. 19, Jul. 1996, pp. 3338–3346.

Webpages downloaded Oct. 15, 1996 at Texas Instruments site–on Digital Light Processing at www.ti/com/dlp/docs/works/faq, 37 pages.

Article entitled Lifetime Estimates and Unique Failure Mechanisms of the Digital Micromirror Device (DMD), by Douglass of Texas Instruments, 8 pages.

Article entitled "Control of Micromachined deformable mirrors" by Agronin et al. for JPL at Calif. Inst. of Technology, 22 pages.

Article entitled "Amputation of static shapes and voltages for micromachined deformable mirrors with nonlinear electrostatic actuators", by Wang et al., 30 pages.

* cited by examiner

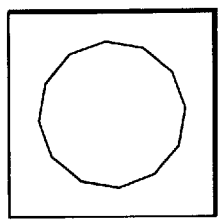
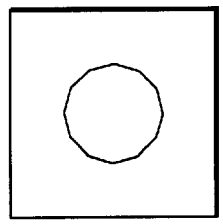
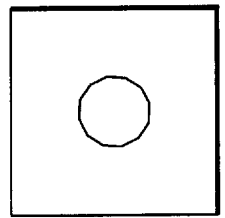
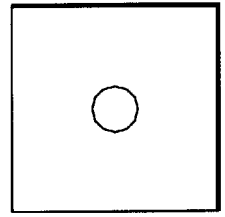
ACTUAL IRIS OPENINGS 12-LEAF
FIG. 3
PRIOR ART
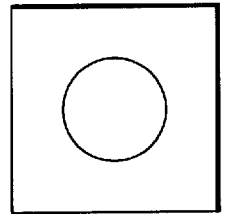
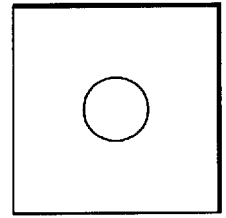
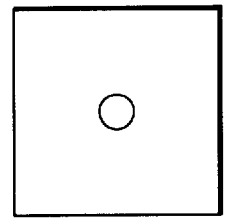
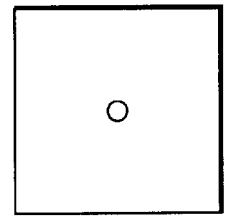
IDEAL IRIS OPENING
FIG. 4

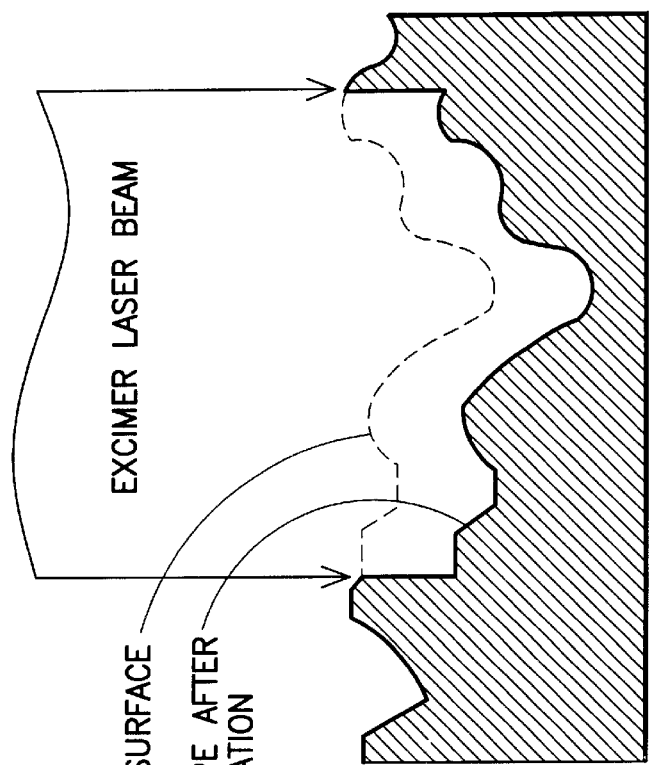
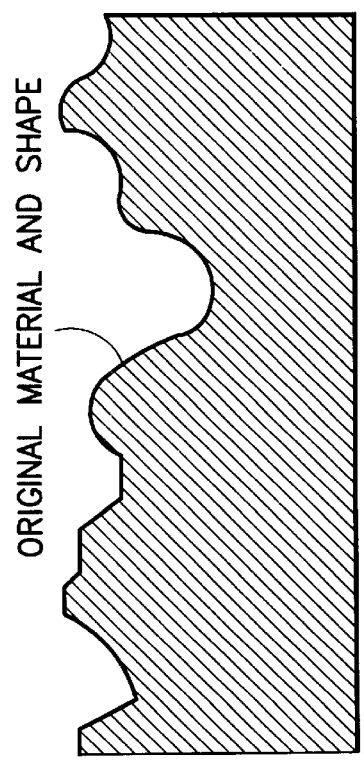

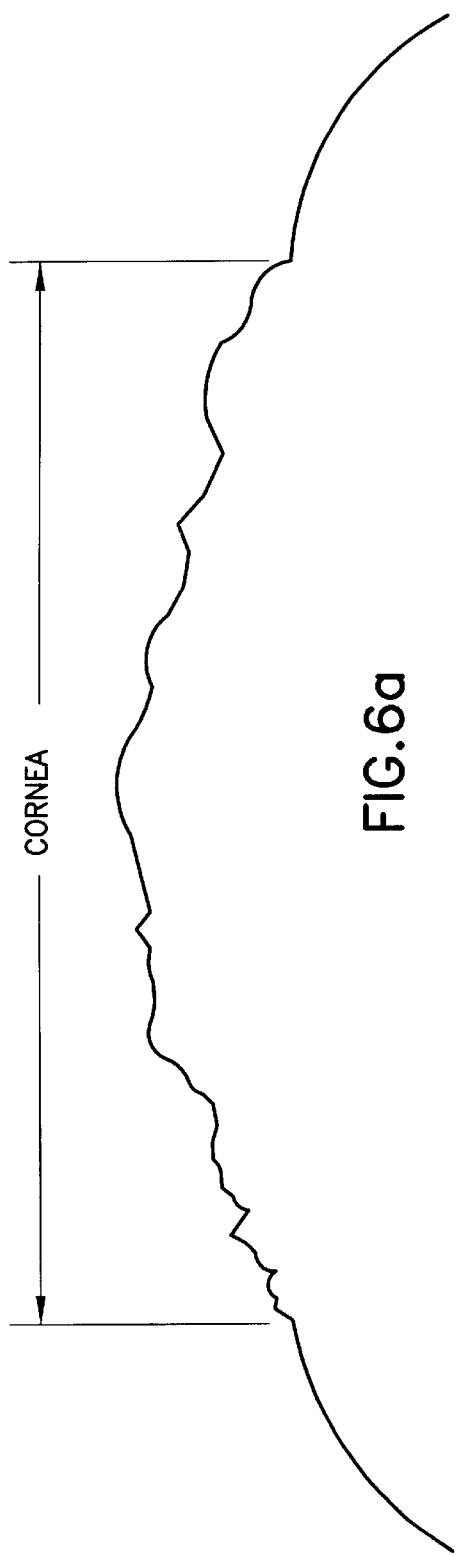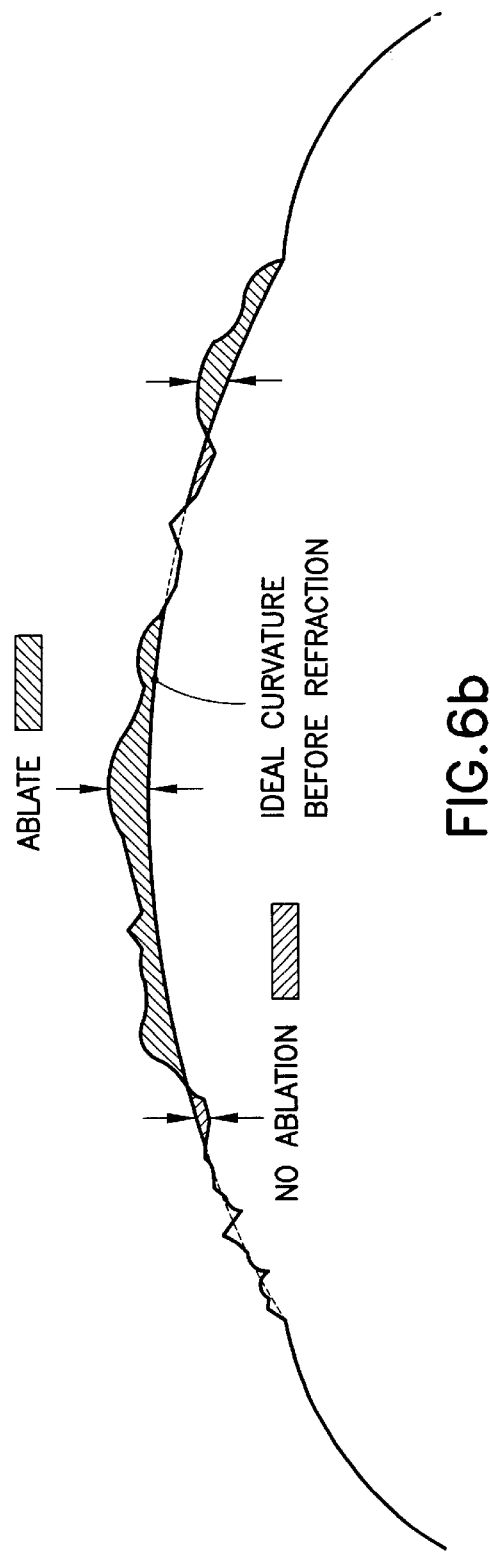

0.5-mm DIA SPOT 1-mm DIA SPOT

SMALL TOPOGRAPHY ZONE

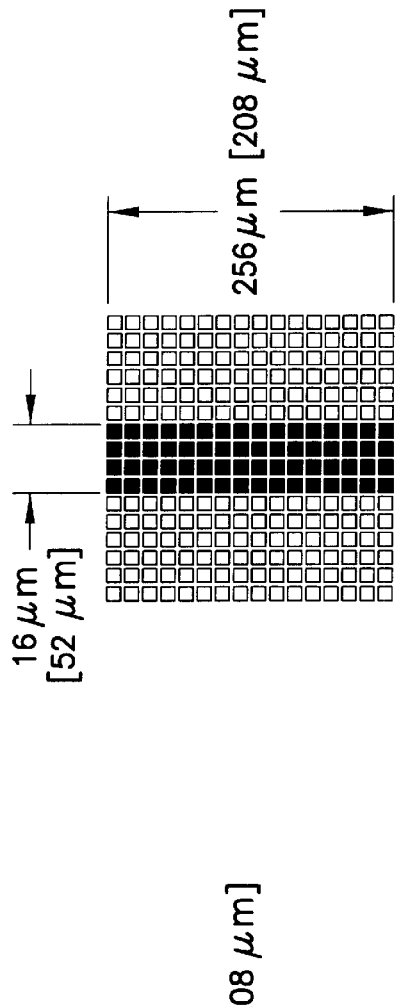
FIG.11
FIG.10
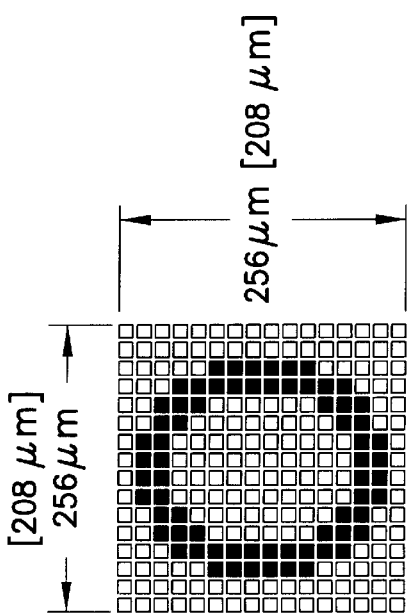
FIG.15

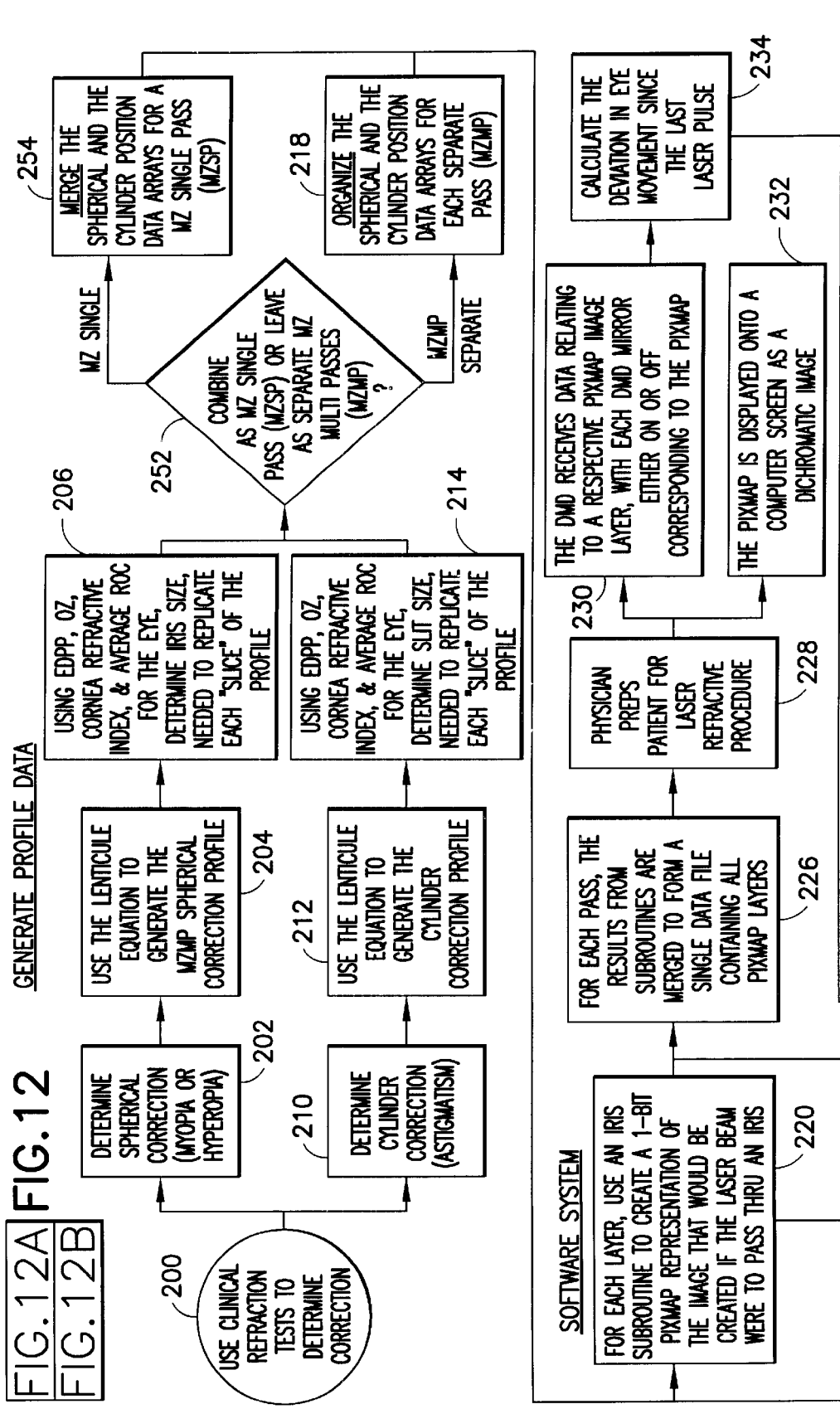

DMD Software : Left Eye
Chart No: 123456

| Data | | | |
|---|---|---|---|
| Chart No. | 123456 | | |
| First Name | | | |
| M.I. | | | |
| Last Name | | | |
| Enhancement | ☐ | | |
| Physician | | | |
| Other | | | |
| Technician | | | |
| Other | | | |
| Procedure | LASIK | μm | 45 |
| Treatment | Myopia | | |
| Eye | Left | | |

Sphere — 207

| Initial Correction | -7.00 | Correction (D) | -7.70 |
| Push (%) | 10 | Vertex Distance | 13 |

Cylinder

| Initial Correction | 0.00 | Correction (D) | 0.00 |
| Push (%) | 0 | Vertex Distance | 0 |
| | | Taper Begin | 3.00 |
| | | Taper End | 4.00 |
| Cylinder Axis | 0 | Cylinder Width | 0.00 |

PTK

| Treatment Zone | 0.00 | Number of Pulses | 0 |
| Etch Depth (μm) | 0.00 | | |

| FIG.14A |
|---|
| FIG.14B |

| Fluence Level (mJ/sq-cm) | 120 |
|---|---|
| Laser Pulse Rate (Hz) | 10 |

Correction Values — 208

| Sphere SLC (D) | -7.70 | Sphere CLC (D) | -6.99 | Sphere Vertex (mm) | 13 |
|---|---|---|---|---|---|
| Cylinder SLC (D) | 0.00 | Cylinder CLC (D) | 0.00 | Cylinder Vertex (mm) | 0 |

Notes

Multi-pass/Multi-zone Values — 209

| Pass--> | Astigmatism | Pre-Treat | Power 1 | Power 2 | Power 3 | Blend | Total |
|---|---|---|---|---|---|---|---|
| O.Z.(mm) | 0.00 | 2.50 | 4.00 | 5.00 | 6.00 | 7.00 | -6.99 |
| C.P. (D) | 0.00 | -2.10 | -3.50 | -2.10 | -1.40 | -0.70 | 100 |
| % of C.P. | 0 | 30 | 50 | 30 | 20 | 10 | 433 |
| Pulses | 0 | 26 | 113 | 109 | 108 | 77 | 74.69 |
| Depth(μm) | 0.00 | 4.43 | 19.43 | 18.77 | 18.71 | 13.36 | |

FIG. 14B

DMD Software : Left Eye
Chart No: 123456

Sphere

| Initial Correction | 0.00 | Correction (D) | 0.00 |
|---|---|---|---|
| Push (%) | 0 | Vertex Distance | 0 |

Cylinder —215

| Initial Correction | -2.00 | Correction (D) | -2.00 |
|---|---|---|---|
| Push (%) | 0 | Vertex Distance | 0 |
| | | Taper Begin | 4.00 |
| | | Taper End | 5.00 |

| Cylinder Axis | 10 | Cylinder Width | 5.00 |
|---|---|---|---|

PTK

| Treatment Zone | 0.00 | Number of Pulses | 0 |
|---|---|---|---|
| Etch Depth (μm) | 0.00 | | |

FIG.16A

| Data | |
|---|---|
| Chart No. | 123456 |
| First Name | |
| M.I. | |
| Last Name | |
| Enhancement | ☐ |
| Physician | |
| Other | |
| Technician | |
| Other | |
| Procedure | LASIK μm 45 |
| Treatment | Astigmatism |
| Eye | Left |

| FIG.16A |
|---|
| FIG.16B |

FIG.16

| | Fluence Level (mJ/sq-cm) | 120 |
|---|---|---|
| | Laser Pulse Rate (Hz) | 10 |

Notes

216 — Correction Values

| Sphere SLC (D) | 0.00 | Sphere CLC (D) | 0.00 | Sphere Vertex (mm) | 0 |
|---|---|---|---|---|---|
| Cylinder SLC (D) | -2.00 | Cylinder CLC (D) | -2.00 | Cylinder Vertex (mm) | 0 |

217 — Multi-pass/Multi-zone Values

| Pass-> | Astigmatism | Pre-Treat | Power 1 | Power 2 | Power 3 | Blend | Total |
|---|---|---|---|---|---|---|---|
| O.Z.(mm) | 5.00 | 0.00 | 0.00 | 0.00 | 0.00 | 0.00 | -2.00 |
| C.P. (D) | -2.00 | 0.00 | 0.00 | 0.00 | 0.00 | 0.00 | 100 |
| % of C.P. | 100 | 0 | 100 | 0 | 0 | 0 | 104 |
| Pulses | 104 | 0 | 0 | 0 | 0 | 0 | 17.89 |
| Depth(μm) | 17.89 | 0.00 | 0.00 | 0.00 | 0.00 | 0.00 | |

FIG.16B

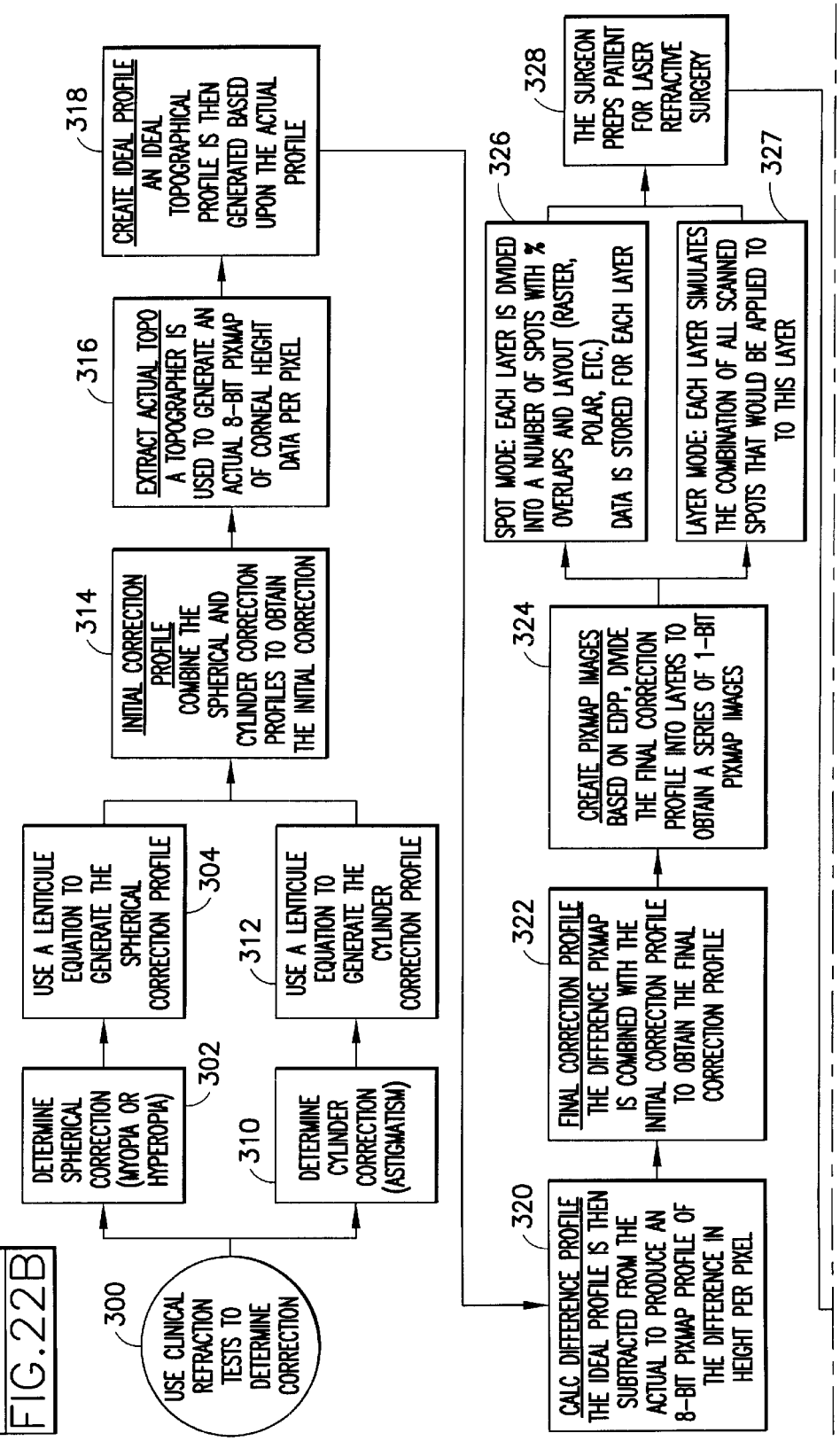

| FIG.25A |
| FIG.25B |

METHOD AND SYSTEM FOR CONTROLLING A DIGITAL MIRCOMIRROR DEVICE FOR LASER REFRACTIVE EYE SURGERY

This application is a continuation-in-part of U.S. Ser. No. 09/524,312, filed Mar. 13, 2000, and which is hereby incorporated by reference herein in its entirety.

The U.S. Government has a paid-up non-exclusive license in this invention as provided for by Grant No. R44 EY11587 awarded by the National Eye Institute of the National Institute of Health.

BACKGROUND OF THE INVENTION

1. Field of the Invention

This invention relates broadly to eye surgery. More particularly, this invention relates to refractive laser systems for eye surgery.

2. State of the Art

The laser refractive surgery (or laser keratectomy) field has rapidly grown over the past few years with many new lasers and algorithms to correct human vision. Systems are now using laser wavelengths from the ultraviolet (excimer) to the infrared to change the shape of the cornea in a calculated pattern which makes it possible for the eye to focus properly. For example, in the treatment of myopia, the excimer laser is used to remove or ablate tissue from the cornea in order to flatten its shape. Infrared (IR) energy is also used by some companies to treat myopia by reshaping the corneal tissue by a "thermal" method as opposed to ablation with the excimer wavelength. The correction of hyperopia is produced by steepening the cornea by removing tissue at the outer edges of the cornea (excimer) or by reshaping the cornea at the outer edges (IR energy). The correction of astigmatism, both myopic and hyperopic, requires the laser to remove or reshape tissue in a more complex pattern.

Initial systems approved by the FDA implement the refractive corrections by a broadbeam approach; i.e., by delivering beam-shaped laser energy based on thin lens theory and paraxial optics applied to a single spherical surface. The beam is shaped by a motorized iris (myopia and hyperopia) and a motorized slit (astigmatism) configured according to profiles derived through Munnerlyn's derivation (C. R. Munnerlyn, S. J. Koons, and J. Marshall, "Photorefractive keratectomy: a technique for laser refractive surgery", *J. Cataract Refract. Surg.* 14, 46–52 (1988)). Referring to FIG. 1, more particularly, an excimer broadbeam laser beam 10, typically having a raw rectangular shape measuring 8–10 mm by 20–25 mm and shaped by optics into a 7–10 mm square or circle, is projected onto a motorized, mechanical iris 12 to create a two dimensional (2-D) circular ablation pattern for treating myopia, and onto a motorized, mechanical slit 14 to create a 2-D rectangular ablation pattern for treating astigmatism, and together forming the combined 2-D pattern 16. Thus, the large rectangular laser beam is shaped to form a circle or a smaller rectangle. These shapes are then projected with an imaging lens 18 onto the cornea 20 of the eye 22 in a controlled manner to perform the refractive correction. To create a refractive correction, a correctly shaped volume of tissue must be removed. Referring to FIG. 2, this volume of tissue is removed by firing a series of laser pulses (1, 2, 3, . . . , n) through the iris and/or slit in a controlled fashion to create a three dimensional (volumetric) etch. This is the most common method in the commercial market today and is currently used by VISX and Summit. Referring to FIG. 3, as a mechanical iris is used to create the "circular" part of the ablation pattern, the etch is not perfectly circular. Physical irises possess a finite number of blades. For example, VISX uses a 12-leaf (12 blades) iris, while Summit used a 14-leaf iris. Therefore, the resolution of the ablation patterns through the iris (FIG. 3) is far from the ideal (FIG. 4). Moreover, the choice of ablation patterns (circular, rectangular, or a combination thereof), is constrained by mechanical limitations.

A more recent approach to laser keratectomy uses a scanning laser spot system in which a small laser spot (typically 0.5 mm to 1.0 mm in diameter) is scanned across the cornea in a predetermined pattern to achieve refractive corrections. These systems differ in that they are more flexible than the broadbeam approach. With the control of a small spot, different areas of the cornea can be shaped independently of other areas. The scanning spot system has the added advantage of being able to ablate smaller regions of the cornea (0.5 to 1.0 mm spot size) so it can be directed to ablate more complex, customized patterns (as opposed to the broadbeam approach).

Recently, corneal topography maps have been used to reveal that the cornea has many minute variations across the cornea. The broadbeam laser approach ablates an equal amount of tissue from the high points and low points of the corneal surface so that the original contour of the surface remains (compare FIGS. 5a and 5b which show exaggerated variations of a greatly enlarged minute location). The broadbeam laser cannot correct these minute variations. Initial scanning spot systems also failed to accommodate surface contours. Yet, the introduction of the scanning spot laser has allowed more controlled treatment and thus corneal topography-driven treatments have been produced. For this procedure, the surface topography of the eye is considered along with the refraction correction profile. Thus, Munnerlyn's equation, or any other higher order model, is combined with the eye surface topography to achieve a better refractive correction. To derive the ablation profile, the corneal profile (topographical data), as shown in FIG. 6a, is first determined from the corneal topography system measurements. Next, the topographical data is compared to the ideal corneal shape, e.g., a sphere or asphere, without correction. Referring then to FIG. 6b, the difference between these two is determined at each x,y point in the cornea topographical data array (a digitized image). Then, a profile which eliminates the topographical data (hills and valleys) is generated leaving an ideal surface after which the refraction correction ablation profile is applied. Alternatively, the topographical differences can be combined into the refraction correction ablation profile and the entire combined profile can be applied all at once. For either method, the scanning spot approach allows treatment in isolated areas (versus broadbeam), and thus a pattern of spots is applied to attempt to correctly match the topography.

The corneal topography approach compensates only for topographical aberrations at the corneal surface. However, the eye is a complex optical system of which the cornea is only one component. Thus, the current refraction correction equation, as derived by Munnerlyn, is not capable of suggesting what correction must be made to the corneal shape in order to optimally correct for the overall aberration of the eye's optical system.

There have been several recent approaches to the above problems. First, by expanding the mathematical equations for refraction correction to include higher order effects, coma (3rd order) and spherical (4th order) aberrations can be reduced. See C. E. Martinez, R. A. Applegate, H. C. Howland, S. D. Klyce, M. B. McDonald, and J. P. Medina, "Changes in corneal aberration structure after photorefractive keratectomy," *Invest. Ophthalmol. Visual Sci. Suppl.* 37, 933 (1996). Second, by improving schematic model eyes to include higher order aberrations, these new models can provide insight into how the various elements of the eye optical system correlate to affect visual performance. For example, there is a general consensus that the negative asphericity of the normal cornea contributes a negative aberration content. The negative aberration is compensated for by a positive aberration contribution from the gradient index nature of the lens. See H. Liou and N. A. Brennan, "Anatomically accurate, finite model eye for optical modeling," *J. Opt. Soc. Am. A,* Vol. 14, 1684–1695 (1997). The convergence of work on modeling the human optical system with more accurate mathematical descriptions for refraction correction has led to the development of advanced ablation profile algorithms that treat the cornea as the first aspheric element in an optical system. See J. Schwiegerling and R. W. Snyder, "Custom photorefractive keratectomy ablations for the correction of spherical and cylindrical refractive error and higher-order aberration," *J. Opt. Soc. Am. A,* Vol. 15, No. 9, 2572–2579 (1998).

Therefore, more recently, a number of wavefront sensing systems are being developed for the scanning spot laser refractive market. In these systems, a visible laser beam, or a number of visible laser beams, is/are directed through the entire eye optical system: cornea, lens, vitreous and retina. The return reflection from the retina is recorded by a CCD camera and analyzed against an ideal wavefront. Thus, the entire optical system is analyzed. The result of this analysis yields a simulation of best acuity for the patient. This data can be used to make an exact contour ablation of the cornea. Regardless of which technique is used, the result is a contour topographical map yielding height information from the current corneal shape to the shape calculated to best improve visual acuity with a scanning spot.

However, there are several problematic issues with all scanning spot systems. First is the issue of treatment time. Scanning spot systems require longer refractive surgery times. The scanning spot is a slower approach since the small laser spot has to be moved over a wide surface (up to 10 mm for hyperopia). The scanning spot system typically delivers several hundred spots per treatment layer, and consequently treatment times are relatively long. The broadbeam approach is much quicker as the entire cornea is treated with each laser pulse, or treatment layer.

Second is the issue of safety. The broadbeam laser is inherently safe from a treatment interruption standpoint because the cornea is treated symmetrically for each pulse; the iris represents a circle and the slit represents a rectangle so that every point on the cornea being treated is treated the same with each laser pulse. If the procedure is interrupted, there will always be some symmetrical spherical correction which can be continued more easily at a later time. However, the scanning spot, with its small spot size, cannot cover the entire corneal surface with one laser pulse. Thus, if an interruption occurs, there is no guarantee of a complete corneal etch for a layer at the point of interruption. Continuation at the point of interruption would be difficult.

Third is the issue of tracking. In the scanning spot system the eye needs to be tracked very carefully in order to deliver the spot to the correct point on the cornea as the eye moves. This is not as much of a problem in the broadbeam system as a broader area of the cornea is treated with each pulse.

Fourth is the issue of surface roughness. Due to the circular cross-sectional shape of the laser spot, the scanning spot technique necessitates overlap of the laser spot as the laser spot is moved in a raster scan (left to right, top to bottom) over the cornea (see FIG. 7). While it is necessary to overlap spots to provide complete coverage for a given ablation zone (a typical 80/20 overlap is shown in FIG. 7), regions of overlap will be ablated at twice the etch depth per pulse. This tends to create roughness in the resulting etch. The roughness of the ablated volume is dependent on the spot overlap and to a lesser extent, the ratio of spot diameter and ablation zone diameter. This problem is not seen in the broadbeam approach.

Fifth is the issue of resolution. The laser spot typically has a diameter of between 0.5 mm and 1 mm. However, corneal topography and wavefront sensor analysis provide detailed information about the required correction to the cornea, and such details may require ablation at a resolution greater than 0.5 mm. For example, referring to FIG. 8a, both corneal topography and wavefront sensor analysis provide images which defines several topography zones requiring ablation. One such topography zone is isolated in FIG. 8b. Yet, referring to FIGS. 8c and 8d, neither a 1 mm spot or a 0.5 mm spot, respectively, are sized to ablate the topography zone at the desired resolution.

In response to the problems associated with the current broadbeam and scanning spot system, U.S. Pat. No. 5,624,437 to Freeman, which is hereby incorporated by reference herein in its entirety, discloses the use of a digital micromirror device (DMD) to redirect a broadbeam laser pulse to the eye. The DMD includes over a million individually configurable mirrors each having a square reflective surface 13 or 16 microns per side. The mirrors are configurable into refractive correction patterns of very high resolution, and the laser energy is reflected by the mirrors into appropriate corrective patterns on the eye. The system has none of the disadvantages associated with prior broadbeam and scanning spot systems, but the advantages of each are provided.

In view of the superior resolution capable with the Freeman DMD laser system, it is desirable to utilize a DMD laser system which is adaptable to perform any type of laser ablative pattern: broadbeam circular and rectangular patterns, scanning spot circular and rectangular patterns, corneal topography patterns, and wavefront sensor analysis patterns.

SUMMARY OF THE INVENTION

It is therefore an object of the invention to provide a DMD-refractive laser system which can recreate in relatively higher resolution any of the ablation patterns currently used in broadbeam and spot scanning systems.

It is another object of the invention to provide a control system for a DMD-refractive laser system which configures the mirrors of the DMD into refractive correction patterns.

It is a further object of the invention to provide a control system which is adapted to permit a DMD to be utilized with current broadbeam lasers, enabling such lasers to refractively correct the optical system of the eye with greater resolution, speed, and accuracy.

It is an additional object of the invention to provide a control system for a DMD-refractive laser system which can be operated in either of broadbeam or scanning spot modes.

In accord with these objectives a laser eye surgery system according to the invention includes a laser for producing a laser beam capable of making refractive corrections, an optical system for shaping and conditioning the laser beam, a DMD for reflecting the shaped and conditioned beam toward the eye, a computer system for controlling the mirrors of the DMD, and an eye tracking system which tracks the position of the eye and provides feedback to the computer system. According to the invention, the computer system includes system software which permits the DMD to emulate the patterns and laser beam control provided in prior art broadbeam systems and scanning spot systems. In view of the above, the laser surgery system is adaptable to perform every currently used approach to laser surgery. That is, as the techniques are controlled by software in the computer system coupled to the DMD, the system is not limited by hardware requirements, and via configuration of the software, a single laser surgery system may be used to operate according to any of the above described approaches. Moreover, the laser surgery system can be coupled to or adapted to receive data from corneal topographers or wavefront sensor systems and utilize such data to increase the quality of correction. Furthermore, the laser surgery system provides much greater resolution than prior art systems as the individual mirrors of the DMD are 13 or 16 microns in size, substantially smaller than the smallest scanning spots.

Additional objects and advantages of the invention will become apparent to those skilled in the art upon reference to the detailed description taken in conjunction with the provided figures.

BRIEF DESCRIPTION OF THE DRAWINGS

FIG. 3 is a schematic of various size openings available with a prior art 12-leaf mechanical iris for defining laser ablation patterns.;

FIG. 4 is a schematic of ideal iris openings for creating laser ablation patterns;

FIGS. 5a and 5b are exaggerated illustrations of corneal topographies before and after broadbeam laser ablation;

FIG. 6a is an enlarged and exaggerated cross-section of a cornea illustrating topographical roughness of the cornea;

FIG. 6b is an enlarged and exaggerated cross-section of the cornea of FIG. 6a in which areas above an ideal curvature are ablated and areas below ideal curvature are not ablated so that a refractive correction etch may be performed thereafter;

FIG. 8b is an image of one of the topography zones of FIG. 8a;

FIG. 10 is a schematic of a DMD mirror array circular pattern;

FIG. 11 is a schematic of a DMD mirror array circular rectangular or slit pattern;

FIG. 14 is an exemplar screen print for a myopic treatment using the software of the DMD laser surgery system of the invention;

FIG. 15 is a schematic of a DMD ring-shaped pattern mirror array for hyperopic refractive correction;

FIG. 16 is an exemplar screen print for an astigmatic treatment using the software of the DMD laser surgery system of the invention;

DETAILED DESCRIPTION OF THE PREFERRED EMBODIMENTS

Figure 9:
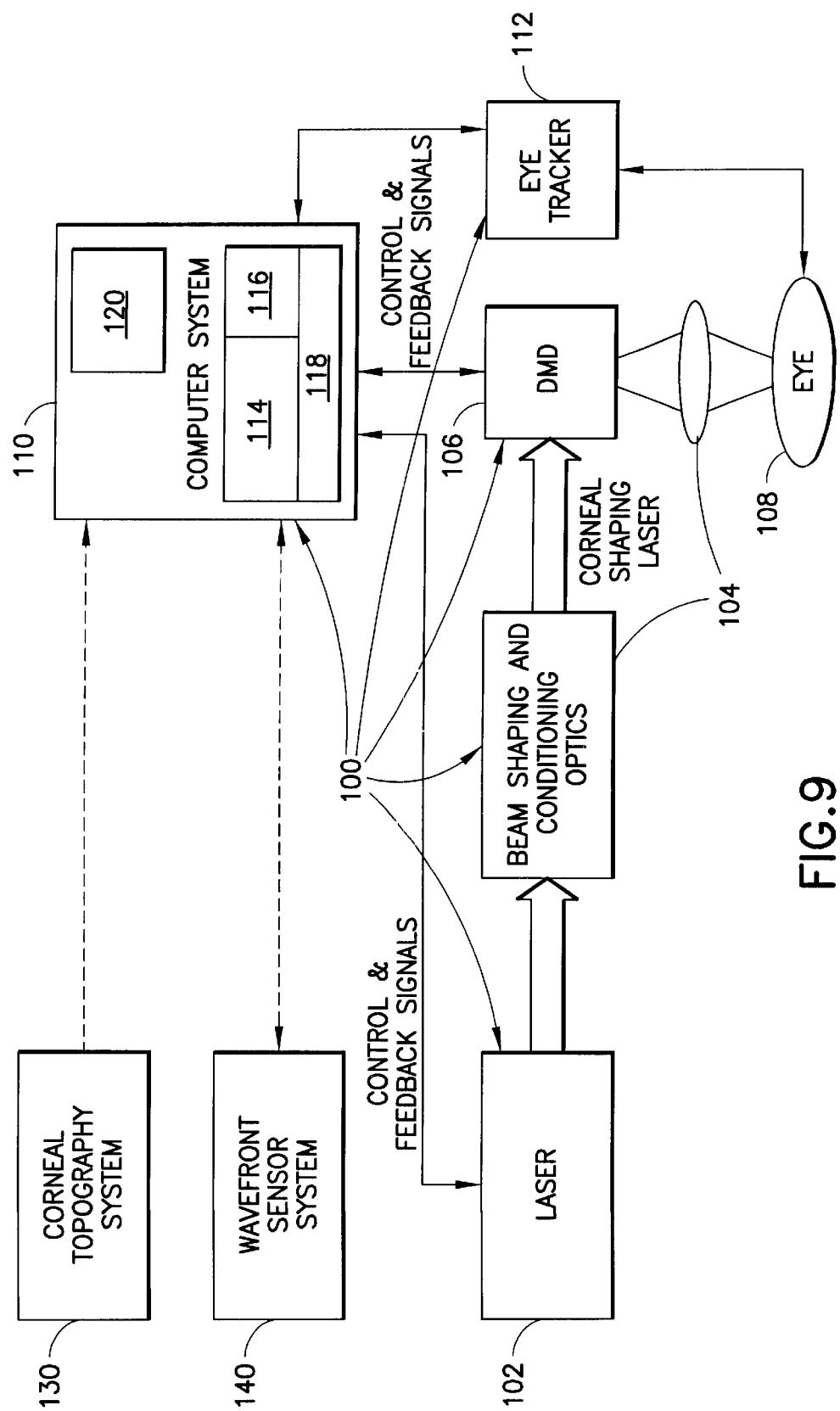
FIG. 9 is a schematic of a DMD laser refractive surgery system utilizing the control system of the invention.

Turning now to FIG. 9, a laser eye surgery system 100 includes a laser 102 for producing a laser beam capable of making refractive corrections, an optical system 104 for shaping and conditioning the laser beam, a digital micromirror device (DMD) 106 for reflecting the shaped and conditioned beam toward the eye 108, a computer system 110 for controlling the mirrors of the DMD 106, and an eye tracking system 112 which tracks the position of the eye 108 and provides feedback to the computer system 110. With the exception of the eye tracking system 112, which is addressed in more detail below, the laser surgery system 100 is substantially similar to the laser beam modulating apparatus disclosed in U.S. Pat. No. 5,624,437, previously incorporated by reference herein.

More particularly, the computer system 110 includes a computer 114 including a microprocessor, a video controller board 116, a DMD controller 118 which is capable of individually manipulating the mirrors of the DMD 106 into either an ON or OFF position, and a video monitor 120. The computer system 110 is capable of controlling the video controller board 116, monitoring and controlling external devices (safety switches, surgery footswitch, shutters, laser interface, etc.), and providing information to the user. A current preferred computer 114 is a Dell Workstation Model 6550, with Dual 550 MHZ Pentium III Xeon Processors, 128 Mbytes of RAM, and 9.1 GByte SCSI hard drive, though other computers can likewise be used. The video controller board 116, e.g., the LCD555PCI video card available from Inside Technology (P/N 710920), supplies video signals to the DMD controller 118 as well as to the video monitor 120. The DMD controller 118 includes a video receiver card, preferably a Texas Instruments, Inc. XGA video receiver card (P/N 4186152-0001), which receives video information from the video controller board 116 and a video driver card, preferably a Texas Instruments, Inc. XGA video driver card (P/N 4186137-0001), which converts the video information into signals that drive the appropriate mirrors in the DMD 106 to the ON or OFF state. The DMD controller 118 may be provided external of the computer 114 or may be provided as a card or set of cards within the computer.

The optical system 104 is provided between the laser 102 and the DMD 106 and is preferably comprised of common, off-the-shelf optical components used to shape the laser beam (this can include beam expansion, collimation and homogenization), direct the laser beam to the DMD 106 for pattern control, and direct the laser beam from the DMD to the corneal surface of the eye. Such optical systems are well-known to those skilled in the art. The DMD 106 is available from Texas Instruments, Inc., and is provided with a UV-transmissive window for excimer-based refractive surgery systems or with an IR-transmissive window for longer IR wavelength refractive surgery systems.

In accord with the invention, software is provided to the computer system 110 which substantially controls the operation of the laser surgery system. The software (a) receives an input from refraction correction tests which identify the type (myopia, hyperopia, or astigmatism) and degree of correction required, (b) generates the appropriate refraction correction profile, (c) generates an ablation pattern for each laser pulse, (d) converts the patterns to control data for the DMD for each layer requiring correction, (e) begins the procedure, (f) tracks the eye position and feedbacks the eye position to the DMD controller, and (g) checks the system parameters and fires the laser when ready. The software is developed under LabView™; however, any suitable language (e.g., C, C++, etc.) can be used for the software development.

The ablation patterns, as described in detail below, may correspond to high resolution emulation of current mechanically created broadbeam patterns, scanning spot patterns, corneal topography patterns, or wavefront-sensor analysis patterns. The ablation patterns are provided by the computer 114 to the DMD controller 118 such that the mirrors of the DMD direct the laser beam to the surface of the cornea in accord with the patterns. In addition, as the patterns are dependent solely upon the software and the DMD, the laser surgery system is preferably adapted to emulate, on demand, any of the broadbeam patterns, scanning spot patterns, corneal topography patterns, or wavefront-sensor analysis patterns, subject to the required data input.

As such, a single laser surgery system can be used by several physicians, each of whom may desire to use a different one of the broadbeam, basic spot scanning, corneal topography and wavefront sensor analysis approaches. All that is required to operate under a selected approach is to direct the software to control the computer system, and thus operate the laser surgery system, accordingly.

Broadbeam Approach

By selecting a broadbeam approach mode of operation, the mirrors of the DMD may be configured by the computer 104 and DMD controller 118 into any broadbeam pattern. Moreover, the DMD, with its 13 or 16 micron square mirrors, has substantially greater resolution and produces a nearly perfect circle when the image is slightly defocused at the eye. The DMD can create a circular pattern (FIG. 10), corresponding to the previously used mechanical iris (FIG. 3), or a rectangular pattern (FIG. 11), corresponding to the previously used slit, by turning ON appropriate mirrors to produce the correct size pattern. It should be appreciated that in FIGS. 10 and 11, only two hundred fifty-six of the million or so mirrors of the DMD are shown.

Figure 12B:
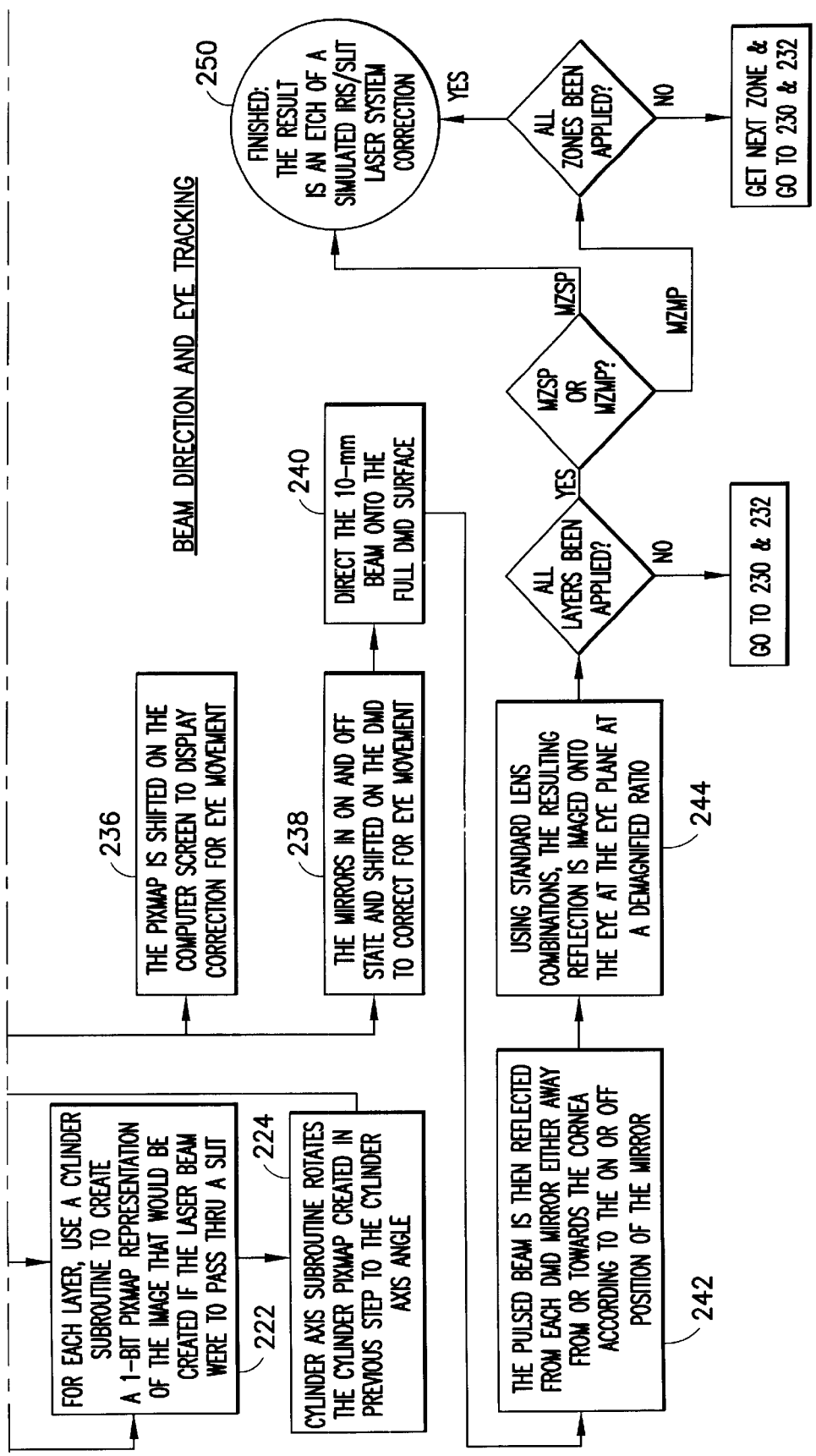
FIG. 12 is a flowchart for using a broadbeam laser system in association with a DMD to correct the shape of the cornea.

Turning to FIG. 12, more particularly, the refraction correction for the eye is recorded in the clinic and values associated therewith are input at 200 into the system in either spectacle or corneal plane values. The software permits value entry in either form and where entry is in spectacle values, the values are converted to corneal plane values by a lookup table based on the distance between the spectacle plane and the corneal plane (typically 12.5 mm).

Figure 13:
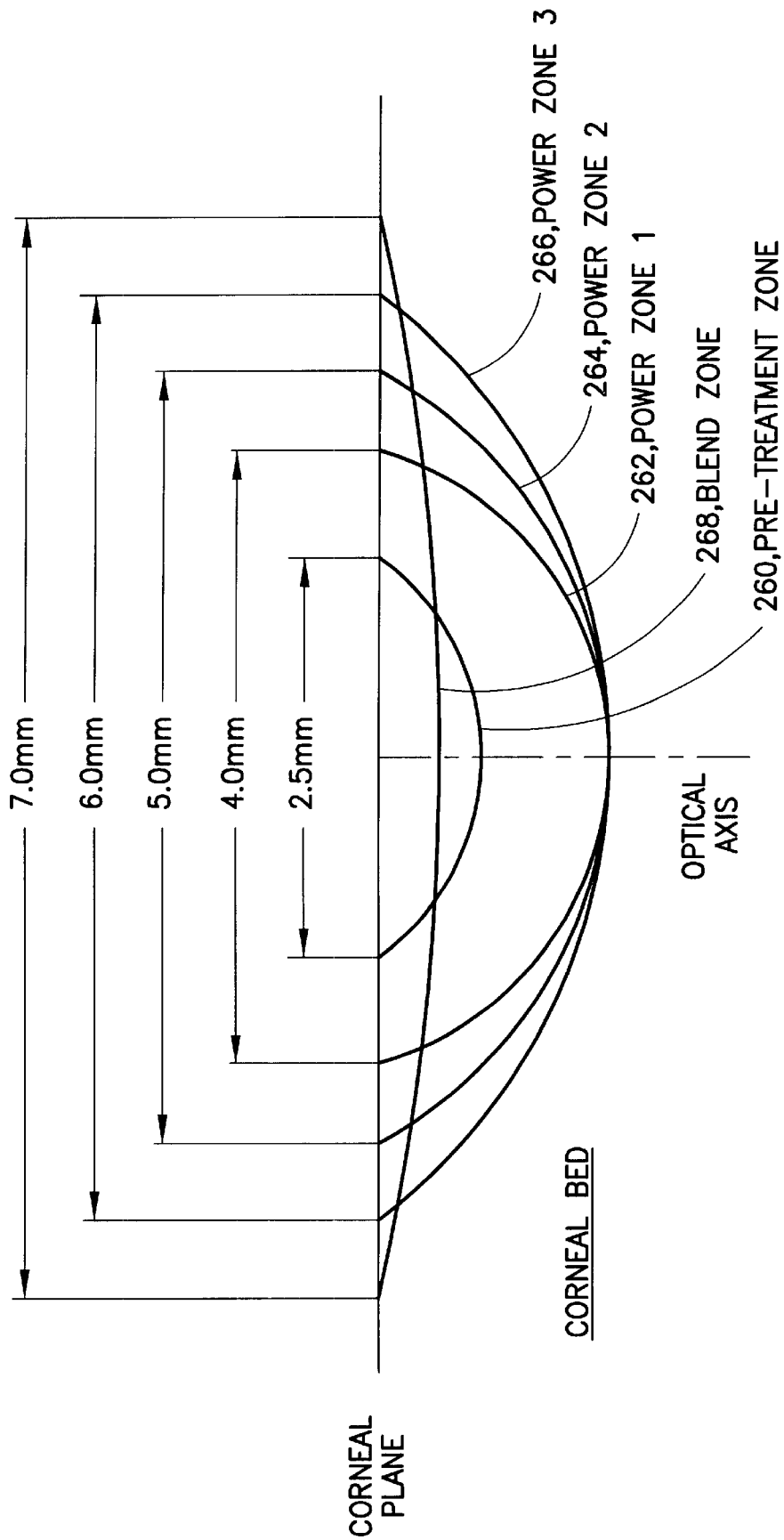
FIG. 13 illustrates the multiple zones used in the multiple zone multiple pass algorithm.

Based upon the clinical refraction at 200, it is determined whether spherical correction (for treating myopia or hyperopia), at 202, or cylindrical correction (for treating astigmatism), is required, or both. For spherical corrections, a multiple zone, multiple pass (MZMP) algorithm (in which each zone is corrected separately) is preferably implemented at 204 with respect to a lenticule equation to more closely approximate the aspherical nature of the cornea. As discussed below, a multiple zone, single pass (MZSP) algorithm may alternatively be implemented by selection at 252. One preferred lenticule equation is a variation on Munnerlyn's first order equation, described below. However, for all refraction correction profiles discussed below, higher order profiles can be implemented. Depending on the refraction correction, a certain number of optical zones are selected for correction. Referring to FIG. 13, these zones are sized 2.5 mm, 4.0 mm, 5.0 mm, 6.0 mm, and 7.0 mm in diameter and centered about the optical axis of the laser beam. The 2.5 mm and 7.0 mm zones are always selected and are termed the pretreatment and blend zones, respectively. The 2.5 mm pretreatment zone is indicated at 260 and is present to reduce/eliminate central island problems; i.e., a central plateau portion of the cornea. The 7.0 mm blend zone is indicated at 268 and is present to provide a less abrupt tissue change between the correction area and the surrounding corneal stroma. The other zones are termed power zones and are used to provide the majority of the refraction correction. Power zone 1 is 4.0 mm in diameter and indicated at 262, power zone 2 is 5.0 mm in diameter and indicated at 264, and power zone 3 is 6.0 mm in diameter and indicated at 266. For cylindrical corrections (astigmatism), only a single power zone (typically 5 mm in diameter) is used to apply a spherical ablation volume to the cornea.

TABLE 1

| | Optical Zones | | | | |
|---|---|---|---|---|---|
| | 2.5 mm OZ | 4.0 mm OZ | 5.0 mm OZ | 6.0 mm OZ | 7.0 mm OZ |
| <3.0 D | (30%) | | | (100%) | (10%) |
| 3.0–6.0 D | (30%) | | (60%) | (40%) | (10%) |
| >6.0 D | (30%) | (50%) | (30%) | (20%) | (10%) |
| Cylinder | | | (100%) | | |

Table 1 describes the optical zones (OZ) used, and the percentages of refraction correction implemented over each optical zone for spherical and cylindrical corrections. With respect to the 2.5 mm zone and the 7.0 mm zone the percentages listed are the percentages of refractive correction which is preferred for correction of the eye, based upon the variation of Munnerlyn's equation. With respect to the power zones (i.e., the 4.0 mm, 5.0 mm and 6.0 mm zone) within each level of correction, the percentages for all of the power zones together total one hundred percent, and individually are the preferred respective refractive correction percentages at the cornea, as inserted into the variation of Munnerlyn's equation, as described below. Particularly, for corrections of less than 3.0 diopters (D), one hundred percent of the correction is applied to the 6.0 mm zone. For corrections from 3.0 D to 6.0 D, sixty percent of the refractive correction occurs in the 5.0 mm zone and forty percent of the correction occurs in the 6.0 mm zone. For corrections of greater than 6.0 D, fifty percent of the correction occurs in the 4.0 mm zone, thirty percent in the 5.0 mm zone, and twenty percent of the correction occurs in the 6.0 mm zone.

For each optical zone requiring correction, the desired depth at a particular radius from the optical axis out to the optical zone diameter can be determined according to the following variation of Munnerlyn's equation, $$Z_{abl}(r) = \sqrt{R_{pre}^2 - \frac{D^2}{4}} - \sqrt{R_{pre}^2 - r^2} + \sqrt{\left[\frac{(n-1)R_{pre}}{\Phi R_{pre} + n - 1}\right]^2 - r^2} - \sqrt{\left[\frac{(n-1)R_{pre}}{\Phi R_{pre} + n - 1}\right]^2 - \frac{D^2}{4}}$$

where $Z_{ab1}(r)$ is the ablation depth of each laser pulse for a given radius r (a known value for a given laser system), $R_{pre}$ is the preoperative radius of curvature and assumed to be 7.86 mm (based on averages), D is the optical zone in millimeters and corresponds to the multiple zones listed in Table 1, n is the index of refraction for the cornea (1.3771), and φ is a lens power defined by the surgeon and is the refraction to be implemented for a zone (i.e., the percentage value from Table 1 for a particular optical zone is used for φ).

By knowing the ablation etch depth per laser pulse at a particular radius, $Z_{ab1}(r)$ (also known as the etch depth per pulse or EDPP), the number of pulses required to complete the procedure is determined. This is done by finding the maximum depth of the ablation which occurs at the center of the optical zone (radius, r=0.0 mm) and dividing by the EDPP; that is, the number of laser pulses required for correction (NLP)=$Z_{ab1}$(0.0)/EDPP. To implement the actual laser ablation, the radius of the "iris" for each laser pulse must be known. From the center of the optical zone, e.g., r=0.0 mm and etch depth=MAX(mm) to the maximum optical zone, where the ablation depth=0.0 mm, values are provided for the equation, and the equation is solved for the radius, r, for each of the laser pulse required to complete the procedure as calculated above (NLP). However, the variation on Munnerlyn's formula cannot be solved in a closed-form solution and thus an iterative approach, e.g., using a zero finder algorithm such as that of Zbrent or Ridder, is used. From the above (that is, once the radius r is known), the "iris" size (i.e., circular pattern size) used for correction of the associated optical zone is determined at 206. The process is repeated for each zone which must be corrected, and an associated "iris" size is calculated for each laser pulse required. An exemplar screen print for a myopic treatment is shown as FIG. 14 and shows the spherical correction required at 207, correction values to implement the correction at 208, and the MZMP values at 209.

Hyperopic treatment profiles are implemented in much the same way at 204 and 206. However, as the tissue must be removed at the outer edges of the cornea, i.e., in the shape of a ring-shaped pattern 5 mm to 10 mm in diameter centered about the optical axis of the laser beam (such that the cornea is steepened), Munnerlyn's equation is used to solve for this correction profile. In another of Munnerlyn's equations (See Charles Munnerlyn, Steven Koons, and John Marshall, "Photorefractive Keratectomy: A Technique for Laser Refractive Surgery", *J. Cataract Refract. Surg.*, Vol. 14, January 1988), the depth of tissue removal, for hyperopia correction, at a distance r from the optical axis is given by:

$$Z'_{abl}(r) = R_{pre} - \frac{(n-1)R_{pre}}{\Phi R_{pre} + n - 1} - \sqrt{R_{pre}^2 - r^2} + \sqrt{\left[\frac{(n-1)R_{pre}}{\Phi R_{pre} + n - 1}\right]^2 - r^2}$$

where $Z_{ab1}'$ (r) is the hyperopic ablation depth of each laser pulse for a given radius r (a known value for a given laser system), $R_{pre}$ is the preoperative radius of curvature and assumed to be 7.86 mm (based on averages), n is the index of refraction for the cornea (1.3771), and φ is a positive lens power (hyperopia) defined by the surgeon and is the refraction to be implemented for the typical 5 to 10 mm zone.

By knowing the ablation EDPP and determining the center, $r_{cent}$, of the hyperopic zone (ending radius minus beginning radius divided by two), the number of pulses (NLP) required to complete the procedure is determined. This is done by determining the maximum depth of the ablation at $r_{cent}$ and dividing by the EDPP; that is, the number of laser pulses required for correction (NLP)=$Z_{ab1}$ ($r_{cent}$)/EDPP. Each radius value for the profile is then found in a similar manner as the described for the myopic correction discussed above. It is noted that there is no removal of tissue at the optical axis, yielding the ring-shaped profile similar to that shown in FIG. 15, but on a larger scale.

This type of ablation cannot be achieved using an iris/slit combination of the prior art. Rather, the prior art requires using a mask or directing an image of the iris/slit opening to the outer areas of the cornea. Both of these methods are difficult to implement. Yet, referring to FIG. 15, it is clear that the DMD can implement a ring-shaped pattern as easily as any other pattern. As such, where hyperopia is treated, data corresponding to sizes of ring-shaped patterns for each zone requiring correction is calculated.

Radius values for the cylinder correction (astigmatism) are determined at 212 and 214 in much the same way as the spherical (myopic) correction at 204 and 206. The cylinder row of Table 1 is used, which indicates that one hundred percent of the refractive correction occurs at one optical zone (typically 5 mm). An exemplar screen print for astigmatic treatment is shown as FIG. 16 and shows the cylinder correction required at 215, the cylinder correction values to implement the correction at 216, and the MZMP values at 217.

A combination of spherical and cylindrical corrections may be required for a particular eye. Therefore, once the sizes for "iris", "slit", and ring-shaped patterns are calculated for the eye, the respective data for the sizes and shapes of corrections are organized, at 218, as a sequence of data arrays representing the order of refractive correction for the cornea for a particular optical zone. For example, it may be desirable to make the entire astigmatic correction prior to any myopic or hyperopic correction. In such case, the data for the astigmatic correction is positioned first, and the data for myopic or hyperopic correction is positioned in a trailing position. Alternatively, the data arrays for the astigmatic and hyperopic or myopic corrections may be interleaved. Regardless, it is preferable that the data for the corrections be provided into data arrays which are associated with the order in which corrective laser ablation patterns are to be provided to the cornea.

Based upon the data arrays and the sequence of the data arrays, images representing the desired ablation profile for the laser beam at each layer of the cornea are created at 220 to 224. More particularly, at 220, for each ablation layer requiring spherical correction, an iris subroutine in the software is used to create a 1 bit or dichromatic multi-pixel image (Pixmap) which emulates that of a prior art mechanical iris or a ring-shaped pattern. Such images are similar to those shown in FIGS. 10 and 15, but will vary in size depending upon the amount of correction and the zone being corrected. At 222, for each ablation layer requiring cylinder correction, a cylinder subroutine in the software is used to create a 1 bit Pixmap which emulates that of a prior art rectangular mechanical slit pattern. Such images are similar to that shown in FIG. 11, but will vary in size depending upon the amount of correction and the zone being corrected. After the rectangular pattern is created, a cylinder angle subroutine of the software is used at 224 to rotate the cylinder Pixmap to the required corrective axis angle. Preferably, the results from subroutines 220, 222, 224 are merged at 226 into a single Pixmap image file for each ablation layer containing data for an image for each pulse of the laser during each pass.

Once the Pixmap images are created, the actual laser surgery procedure can begin. Generally, the patient is placed under a microscope and positioned correctly for the procedure and the physician preps the patient at 228. Prepping includes using a photorefractive keratectomy (PRK) or laser keratomileusis in situ (LASIK) technique. That is, in either technique the corneal stroma must be exposed prior to providing a laser beam to the cornea for corneal reshaping. In PRK, the epithelium of the cornea (approximately 40 to 55 microns) is removed by any effective means, e.g., with a laser, by scraping, or by chemical means, to expose the endothelium. In LASIK, a flap is cut approximately 120 to 160 microns deep into the corneal stroma, and the flap is flipped back to expose the corneal stroma. The physician then reviews the treatment profile and begins the procedure.

The software then translates the Pixmap images into DMD mirror position data. At 230, the DMD receives the data and individual mirrors of the DMD are identified to be in respective ON or OFF positions such that together the mirror array forms a pattern which simulates the Pixmap image. As stated above, when the patterns produced by the mirrors are slightly defocused on the cornea, the patterns are of very high resolution and substantially greater resolution than the patterns defined by the prior art mechanical devices.

At the same time, the software causes the Pixmap image to be displayed at 232 on a video monitor as a dichromatic image, e.g., black and white, so that the physician may review and monitor the ablation patterns.

The eye tracking system 112 provides at 234 input to the computer 110 which then directs the DMD controller 118 to compensate for the deviation of the eye from center (or from a prior registered off-center location). The feedback from the eye tracking system causes the Pixmap image to be shifted at 236 on the video monitor, and the ON/OFF pattern of mirrors is also shifted at 238 to compensate for eye movement such that the DMD mirror ablation pattern is always correctly directed toward the cornea. Various systems may be used to track the movement of the eye and provide feedback to the computer 110 and the DMD controller 118. In one approach, disclosed in U.S. Ser. No. 09/371,195, filed Aug. 10, 1999, and hereby incorporated by reference herein in its entirety, the eye tracking system 112 uses a CCD camera connected to the surgical microscope, an illuminator to illuminate the eye, and an algorithm to find the center of the pupil and compare it against the starting point of the procedure. The eye tracking system 112 is able to continually feed the eye movement information to the computer 110 in order to offset the refraction correction pattern created by the mirrors of the DMD 106 such that the pattern is directed to the correct position based on the eye's last position. Other approaches to tracking the eye may also be used. For example, and not by way of limitation, target markers placed on the cornea (reflective or absorptive to certain wavelengths) may be monitored, laser spots aimed at the cornea (typically infrared energy) and monitored by a camera or other electronic means (such as quad detectors) may be tracked, anterior physiological structures, such as the limbus, may be tracked, or the retina may be tracked.

In parallel with the operation of the eye tracker 112, the computer system checks all of the system parameters (including, but not limited to, laser status, safety switch status, gas cabinet sensor status (for gas-based lasers), safety shutter subsystem status, laser energy sensor status, nitrogen flow status, surgeon footswitch status, emergency stop switch status, surgeon joystick control status, exhaust plume tube position, and status indicator lights). Once the system checks have all been confirmed, the surgeon is able to fire a laser pulse (typically via operation of a footswitch).

When the laser 102 is fired at 240, it is shaped and conditioned by the optical system 104, and directed onto the mirror array of the DMD. The laser beam is then reflected at 242 by the mirror array. Each mirror either reflects its associated portion of the laser beam pulse either away from or towards the cornea according to the respective ON or OFF position of that mirror. As such, the desired ablation pattern is reflected toward the eye. Additional optics then image at 244 the patterned laser beam onto the eye, preferably in a demagnified ratio.

This procedure continues at 230 and 232 for subsequent layers of ablation until all layers (pulses) have been delivered for a given optical zone being corrected. Then, in an MZMP procedure, the required correction to the other zones are implemented on the patient cornea in subsequent respective "passes" (i.e., pulses of the laser on an associated DMD mirror pattern), preferably with a slight pause between each pass for inspection of the eye.

Figure 17:
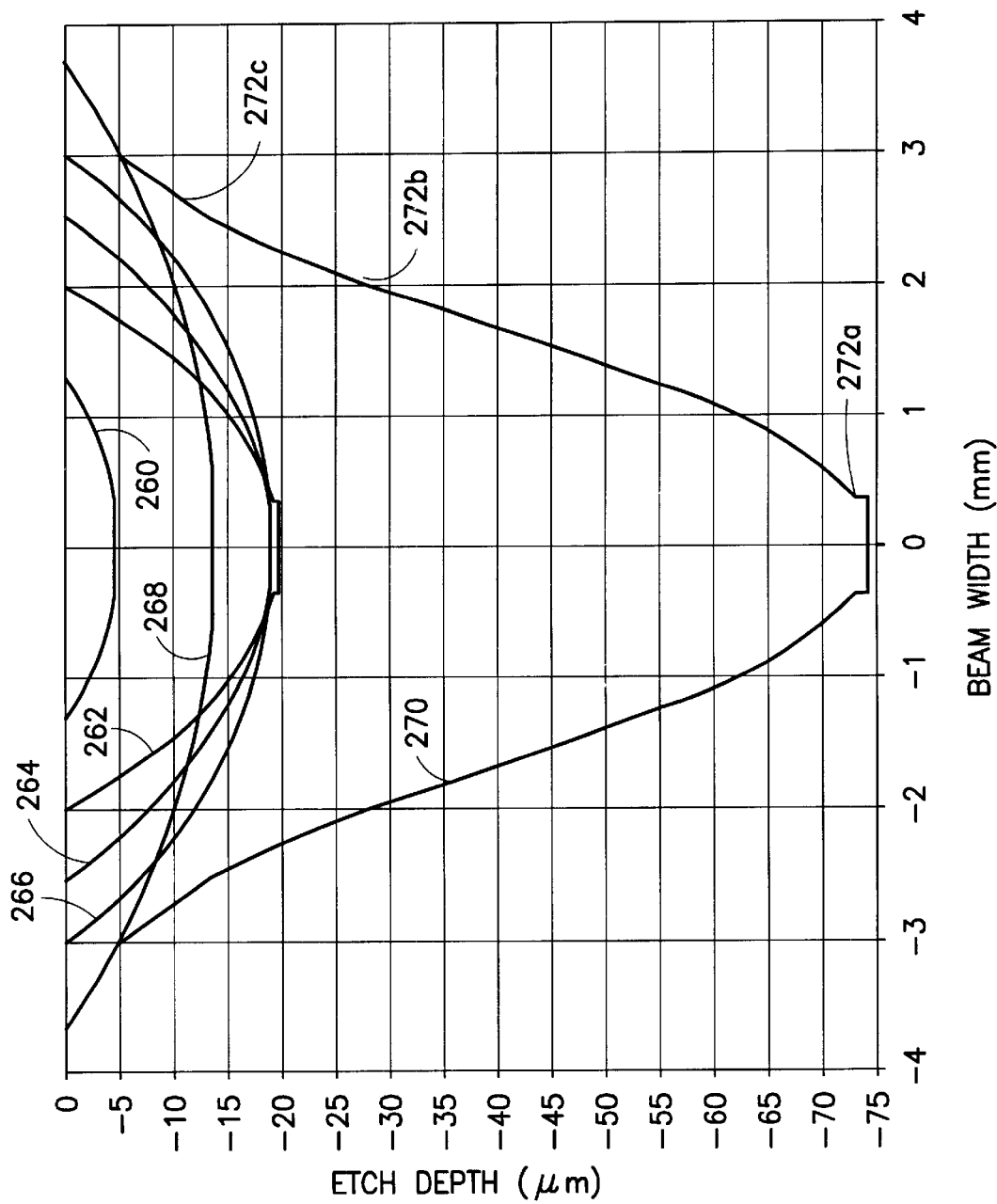
FIG. 17 is a screen print illustrating the volumetric ablation resulting from a multiple zone, multiple pass algorithm.

At the conclusion 250, the resultant etch is aspheric in shape, and represented by the chart of FIG. 17, in which the ablation for the individual zones is illustrated in light lines (2.5 mm pretreatment zone at 260, 4 mm power zone at 262, 5 mm power zone at 264, 6 mm power zone at 266 and 7 mm blend zone at 268), while the total ablation resulting from the combination of individual zones is illustrated in a bold line at 270.

While a MZMP approach has been described above for the broadbeam emulation, alternatively, the Pixmaps for the DMD pattern generation can be defined to ablate across multiple zones in each pass. To that end, at 252 in FIG. 12, the multiple zone, single pass (MZSP) approach may be selected. Upon selection of the MZSP approach, the spherical and cylinder position data arrays for each zone are merged into a single array representing a combination of all of the treatment zone profiles. In accord with one manner of implementing the MZSP approach, all zones and their profiles are merged, by summing, into the graph curve 270 of FIG. 17. However, the graph curve 270 has a plurality of transition points 272a, 272b, 272c which it is desirable to eliminate (i.e., smooth over). These transition points are not as severe as those created with prior art irises and slits in a broadbeam approach. Nevertheless, any transition point may subject the corrected eye to glare or halo effects.

Figure 26A:
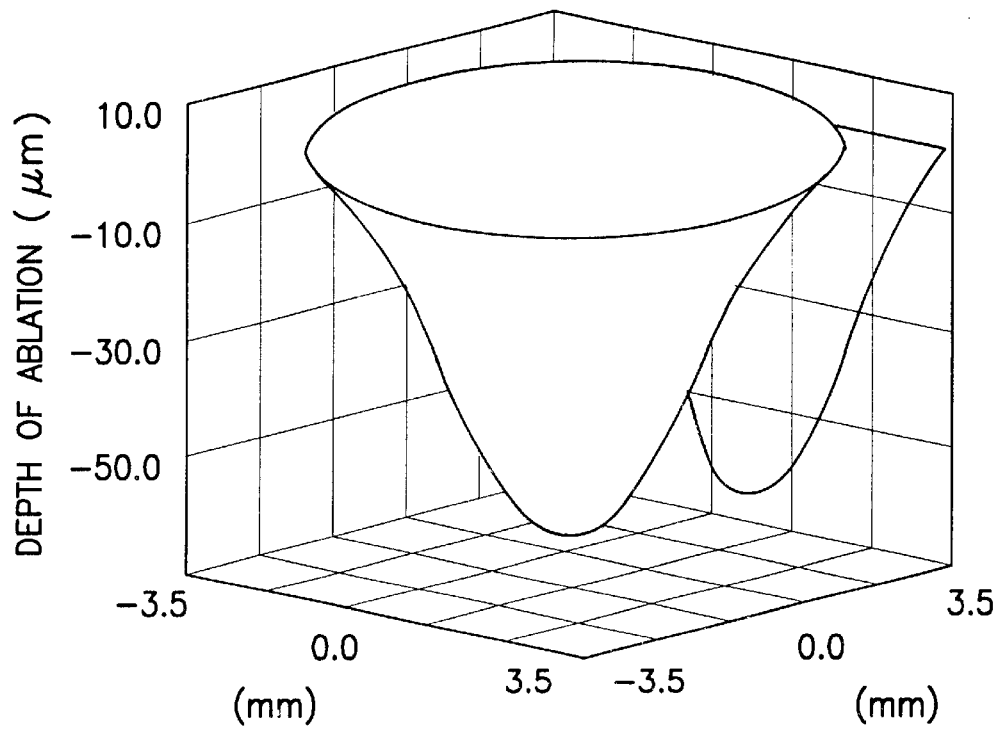
FIG. 26a illustrates a 3-D ablation image according to a preferred multizone single pass (MZSP) broadbeam approach.
Figure 26B:
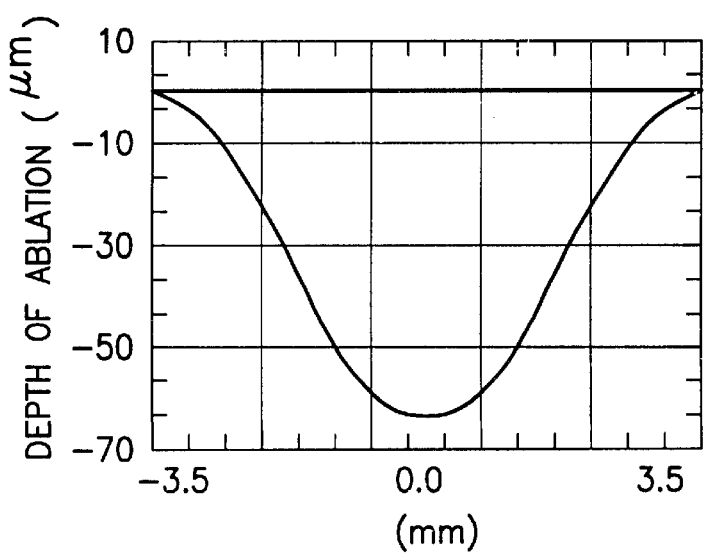
FIG. 26b illustrates a smooth ablation profile according to a preferred MZSP broadbeam approach.
Figure 27:
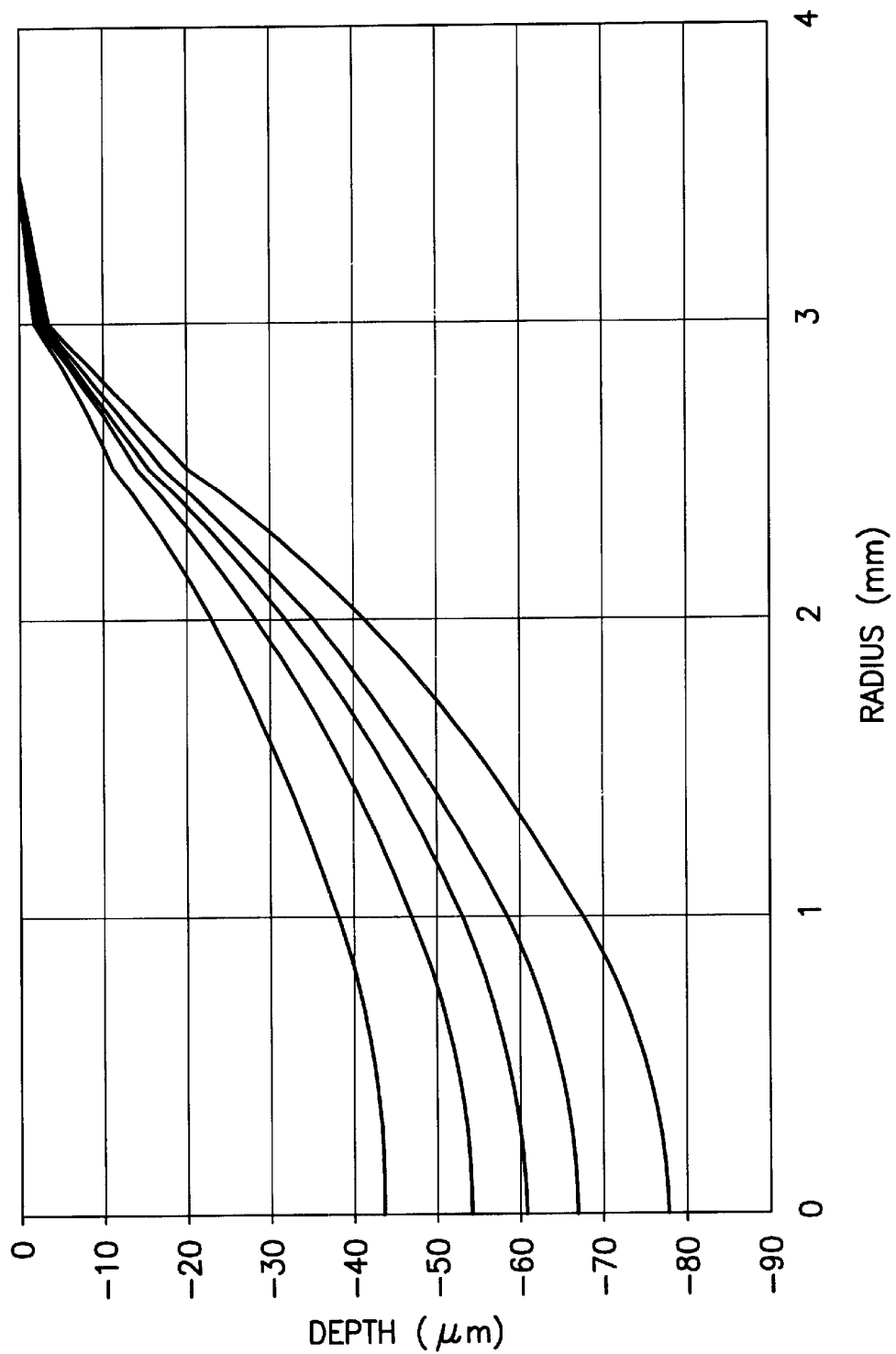
FIG. 27 is a graph illustrating profiles of classifications of degrees of corrections.
Figure 28:
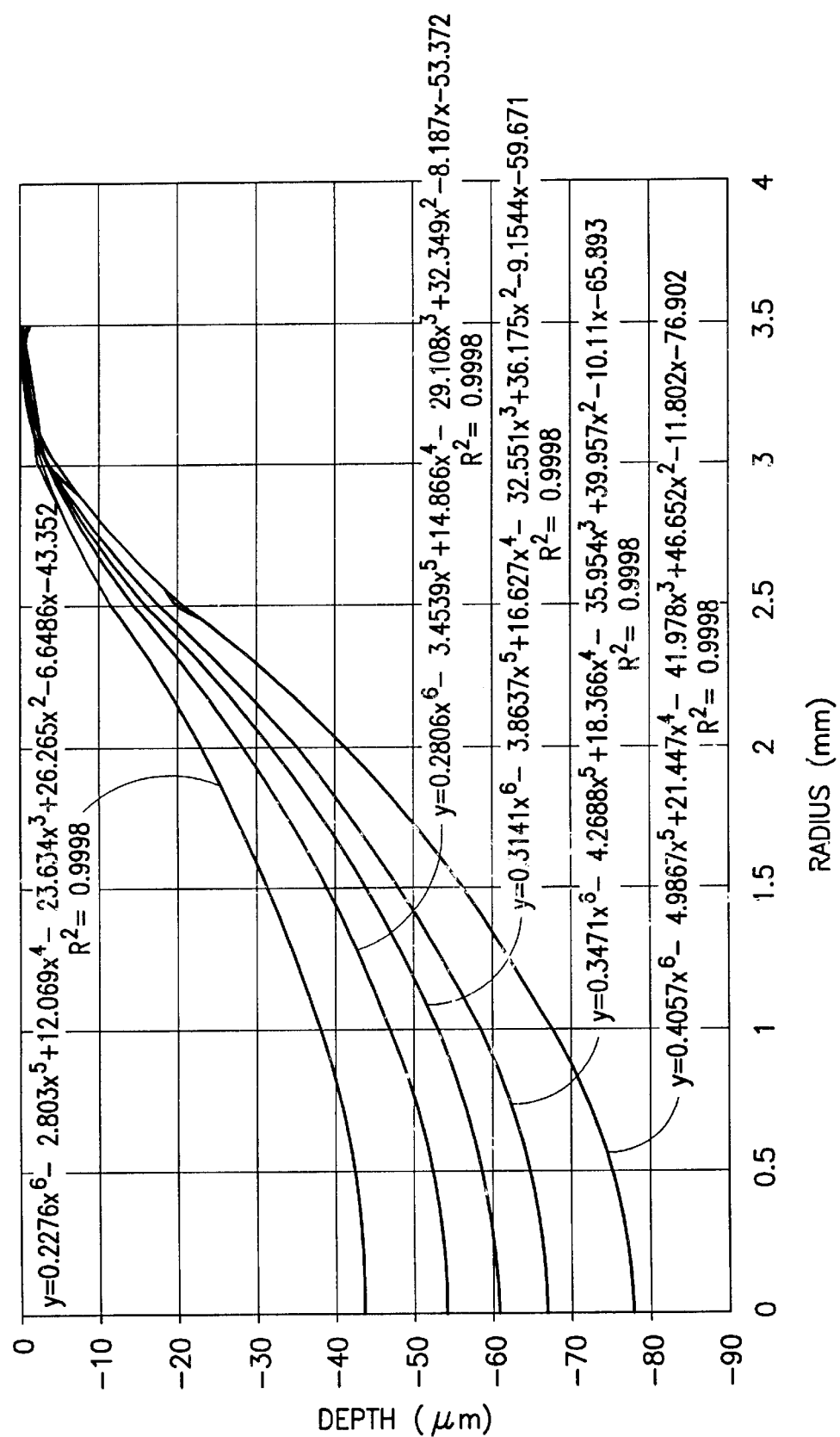
FIG. 28 is a graph illustrating sixth order of magnitude trendlines which follow the contours of the profiles of FIG. 27.
Figure 29:
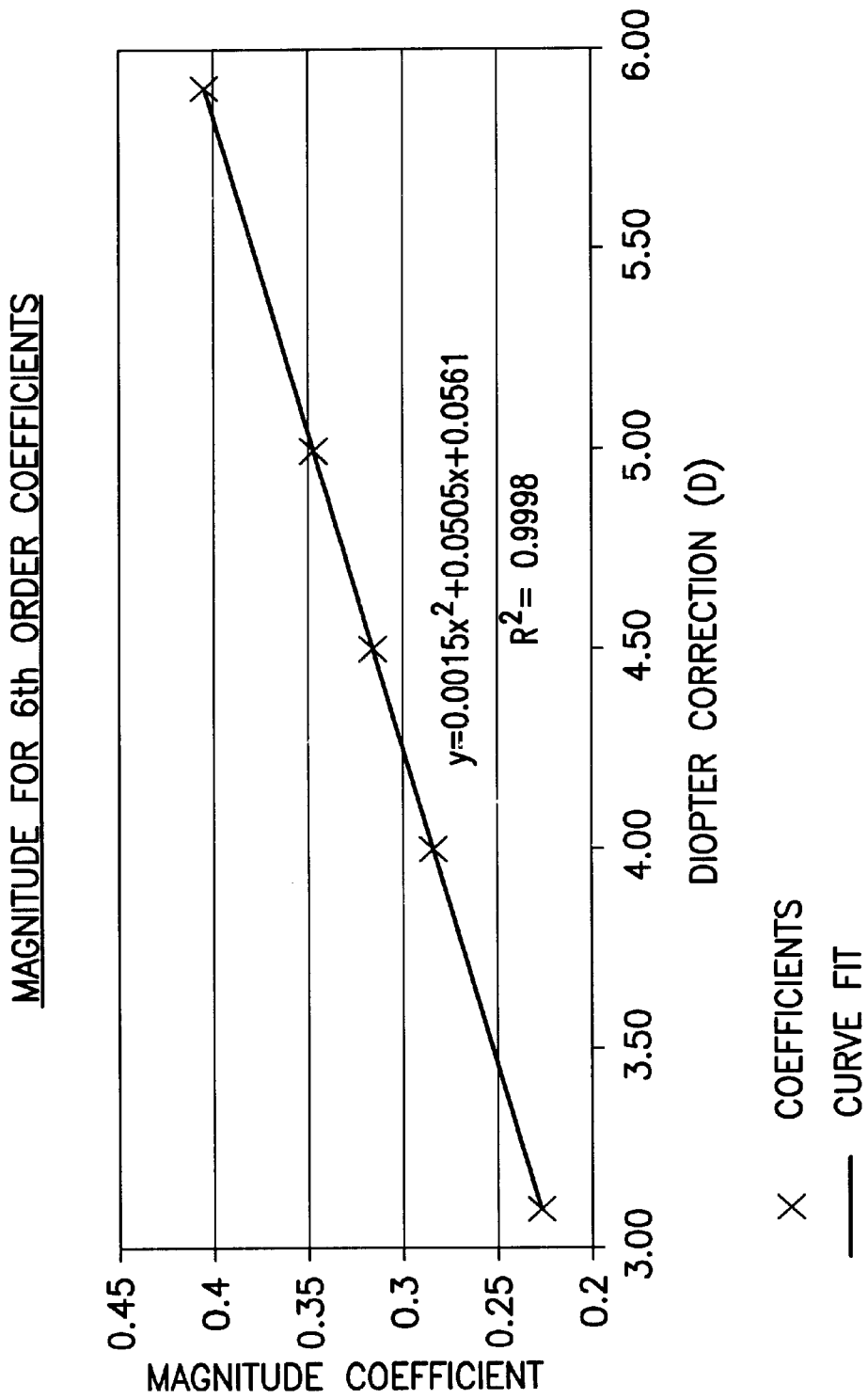
FIG. 29 is a graph illustrating the substantially linearity of the trendlines for the sixth order magnitude equations for each classification based on diopter correction, and a polynomial equation based on thereon.

Therefore, for a MZSP approach, it is more preferable that a curve associated with the resulting graph curve 270 be generated in which a very smooth ablation profile without transition points is provided, such as shown in FIGS. 26a and 26b. In accord therewith, a second manner of implementing the MZSP approach is provided in which a dynamic polynomial equation mimics the multizone profile, but is based solely on the refractive correction (diopter). The dynamic polynomial equation is determined by first classifying required corrections according to their severity. For corrections more severe than −6 diopters, the multizone method uses five zones (including the pretreatment and blend zones), for corrections between −3 diopters and −6 diopters four zones are used, and for corrections less than −3 diopters three zones are used. Referring to FIG. 27, for each of the three classifications of correction severity, several profiles are generated that cover the full range of that classification. Second, a graph compiling the data into a format that can be translated for establishment of a trendline is created. This can be done with any of several software packages, such as Microsoft Excel® or National Instruments Hi-Q™. Third, as shown in FIG. 28, a trendline is established for each of the profiles. The equations for the trendlines (shown in FIG. 28) must closely follow the contours seen in FIG. 28. Polynomial curve fit equations are preferably used for the trendlines, although other curve fits, e.g., the error function erf(r), may be used as well. It has been found that sixth order polynomial equations accurately generate the required profiles. Each equation represents the profile of a specific correction (diopter), and the equations are dissected and the magnitude of each equation order component is graphed based on the correction, with the magnitude of each equation order component found to be nearly linear ($R^2$=0.9993), as shown in FIG. 29. Then, as also shown in FIG. 29, a second polynomial equation is created based on the trendline. One such polynomial, the second order equation $y=0.0015x^2+0.0505x+0.0561$, is shown in FIG. 29, provides a desirable fit. From this second polynomial equation, software is written to generate a dynamic equation that generates a smooth profile based on the desired diopter correction, and the ablation layers are slices through the generated smooth profile. The software may be applied to a DMD in which a central mirror element of the DMD is selected and the radial distance values for each of the other mirrors elements is determined relative thereto. All of the values are then represented in a mathematical array as a data file, and the procedure is then implemented in a similar manner to the previously described MZSP approach to produce a 3-D ablation image (FIG. 26a) and a 2-D ablation profile (FIG. 26b) which is smooth along its length; i.e., without transition points.

In addition, while the spherical and cylinder data arrays are used to create the Pixmap images, the signals used to otherwise control iris and slit motors may be directly utilized and translated into the Pixmap image data. As such, a broadbeam approach with a DMD is highly adaptable, with configurations based upon physician requirements without the mechanical limitations of the prior art.

Scanning Spot Approach

Figure 7:
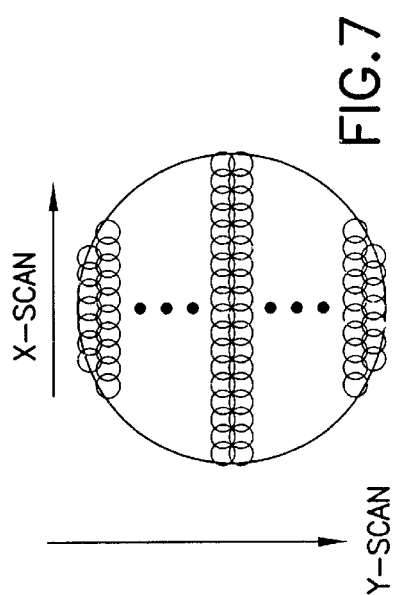
FIG. 7 illustrates the raster scan operation and spot overlap of a scanning spot laser system.
Figure 18:
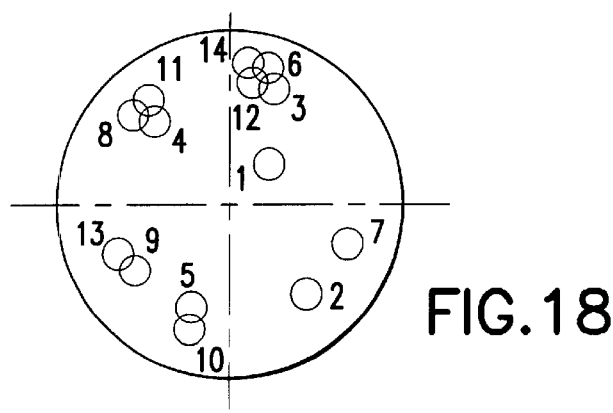
FIG. 18 illustrates a random scanning method for emulation of a scanning spot laser system with the laser surgery system of the invention.
Figure 19:
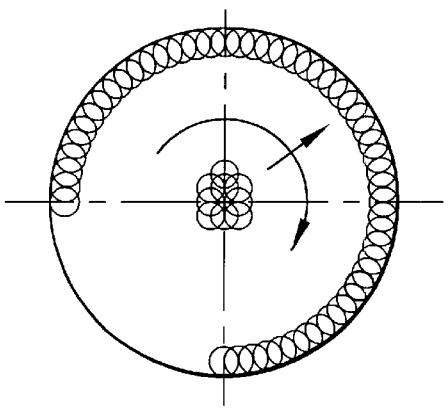
FIG. 19 illustrates a polar scanning method for the DMD laser surgery system of the invention.
Figure 20:
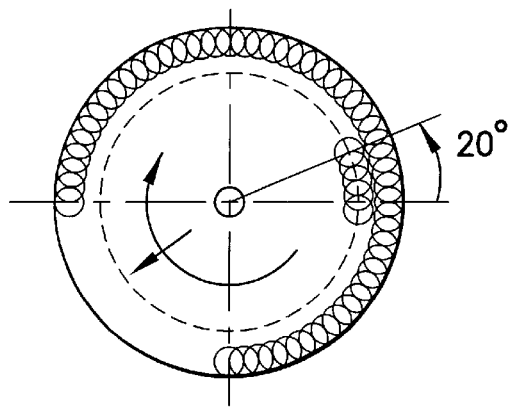
FIG. 20 illustrates a polar scanning method with rotation for the DMD laser surgery system of the invention.
Figure 21:
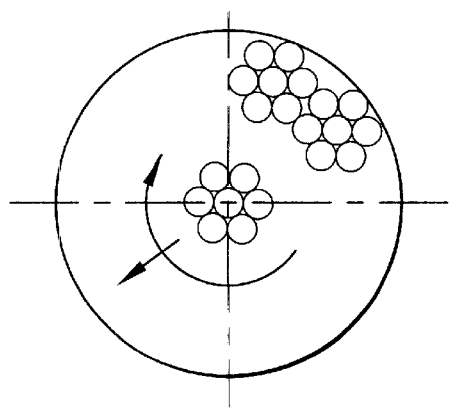
FIG. 21 illustrates a closed-pack scanning method for the DMD laser surgery system of the invention.

By selecting the scanning spot mode of operation, more complex, customized ablation patterns may be applied to the cornea. If the Munnerlyn approach is coupled to the previously described "iris" and "slit" patterns, in either a MZMP or MZSP format, a circular (spherical myopia or hyperopia) or rectangular (astigmatism) ablation pattern will be applied to the eye. Referring back to FIG. 7, the most widely used scan technique for directing a spot scan in accord with an ablation pattern is a raster scan, much like a television monitor scan (left to right, top to bottom). FIG. 18 illustrates another currently used scanning method called a random scan in which the laser spot is moved in a random sequence about the cornea. This scanning method reduces any potential adverse heating effects due to the spots being applied too near to each other. FIG. 19 illustrates a new technique according to the invention, termed a polar scan. In a polar scan, the spot is scanned in a circular fashion for each pulse layer. Preferably, the spots are moved in a 50/50 overlap, though other percentage overlaps may be used. This approach matches the edges of the circle better than the raster approach. FIG. 20, also a new technique, illustrates a polar method with the addition of a rotation (here shown at 20°, though other rotational angles may be used). As such a plurality of sectors are scanned in succession. FIG. 21, yet another new technique, illustrates a closed-pack method in which a hexagonal approach is used to cover an area more efficiently. Preferably, in a closed pack, there is no overlap of the laser spots. In any of these methods, the overlap of the spots may be adjusted to optimize the resulting etch profile and scanning may occur from the center outward or from the periphery inward.

The software enables the DMD to emulate any of the corrective eye patterns and scanning spot methods (raster, random, polar, closed-pack, and others not described) used in a conventional scanning spot approach, in either of two modes.

In a first mode (spot mode), the scanning spot approach can be emulated by turning ON enough mirrors (e.g., a 30 by 30 to 60 by 60 array of mirrors) to create a typical scanning spot laser diameter (e.g., 0.5 mm to 1.0 mm). Alternatively, fewer mirrors can be turned on such that the "spot" is much smaller than typical scanning spots and substantially better resolution can be achieved. This "spot" is then moved across the cornea in any scanning method (e.g., raster, random, polar, polar with rotation, and closed-packed) by turning ON and OFF the appropriate mirrors to simulate offset or scanning of the spot across the DMD device.

In a second and more preferred mode (layer mode), the software directs the DMD to implement an entire ablation layer in a single laser pulse, by turning ON the appropriate mirrors to simulate the resulting etch pattern which would otherwise be created after all scanned spots have been delivered for a particular ablation layer in the spot mode. In this manner, any concern present regarding the effects of interruption of conventional scanning spot system are eliminated, as an entire layer is ablated at once.

Figure 22B:
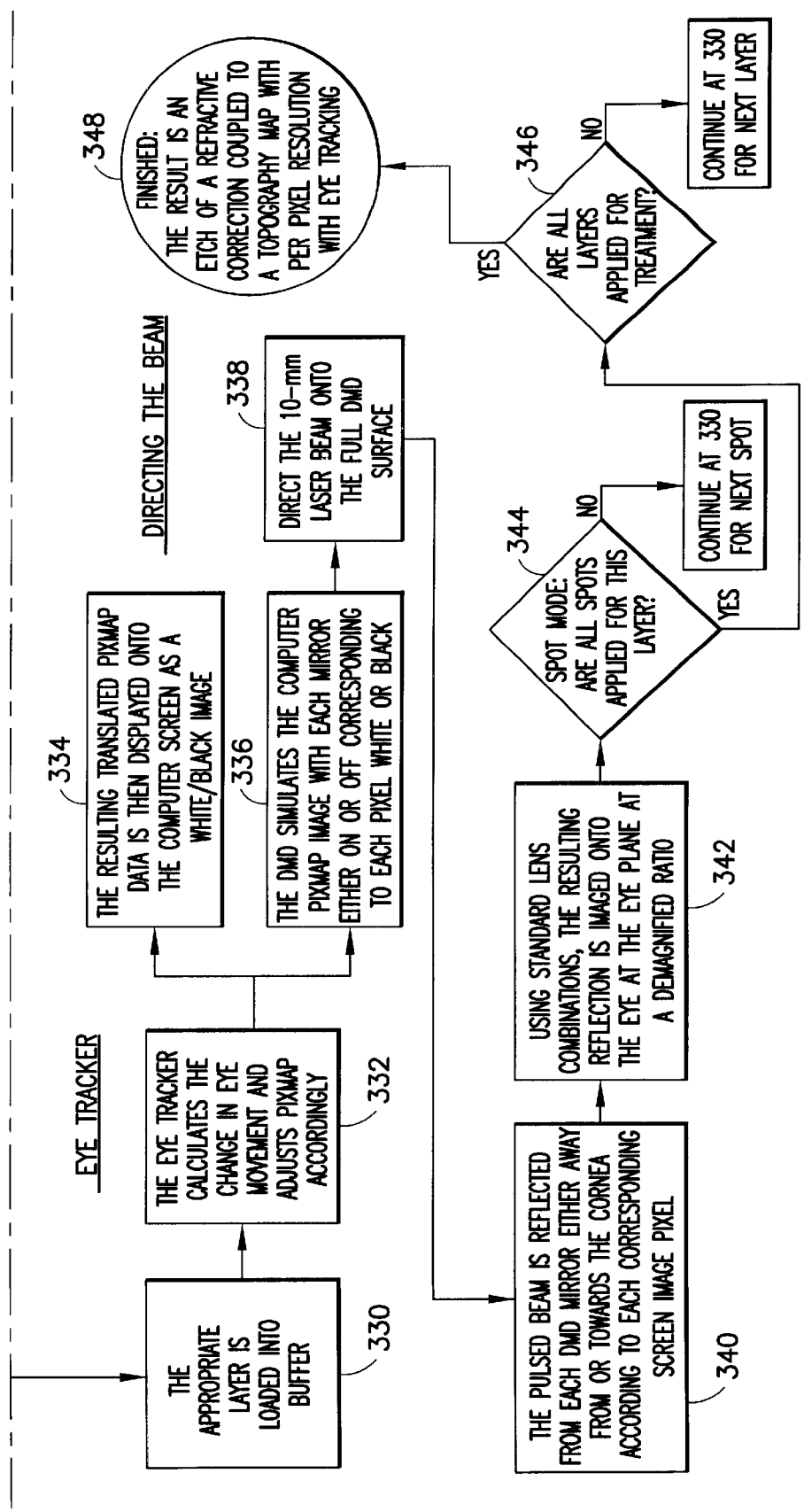
FIG. 22 is a flowchart for emulating a scanning spot approach with the laser surgery system and a corneal topographer.

More particularly, referring to FIG. 22, the scanning spot emulation method is initially similar to the broadbeam approach. That is, clinical refraction tests are carried out at 300 to determine the degree of correction needed. Next, the spherical correction is determined at 302 and a lenticular equation (first or higher order) is used to generate at 304 a spherical correction profile. Likewise, a cylinder correction is determined at 310 and a lenticular equation is used to generate at 312 a cylinder correction profile.

The spherical and cylinder correction profiles are combined to result in an initial correction at 314. Preferably, though not required, the scanning spot emulation additionally accounts for corneal topography data. As such, a topographer 130 (FIG. 9), e.g., a Keratron Corneal Analyzer manufactured by Optikon 2000 of Rome, Italy, is used at 316 to determine the actual topography of the cornea. The topographer generates a Pixmap image of corneal height data at each pixel of the image. The Pixmap image is preferably 8 bit, through other resolutions may be used. Based upon the actual topography of the cornea, an "ideal" topographical profile is generated at 318. The ideal profile corresponds to an ideal spherical or aspherical fit provided by the topographer through mathematical modeling. The difference between the actual profile and the ideal profile is then calculated at 320 to produce a difference profile. The difference profile is a Pixmap image indicating the difference in height between the ideal and actual profiles at each pixel. Next, the difference profile is combined with the initial correction profile to result in a final correction profile.

Based upon the etch depth per pulse (EDPP), Pixmap images are then generated at 324 for each etch slice or layer from the final correction profile. The Pixmap images for each layer are 1 bit images, and data associated with a sequence of the Pixmap images corresponding to the entire laser ablation procedure is stored in memory in the computer system.

Where the system seeks to directly emulate a spot scanning system (i.e., such that each laser pulse ablates a single pixel-sized spot of a layer), each Pixmap image is divided at 326 into a number of spots with a particular percentage overlap and spot layout (raster, random, polar, closed-pack, etc.), which is also stored as data. Where moving spot emulation is not desired (i.e., such that an entire layer will be ablated for each laser pulse), no such division is required and step 327 is implemented.

At this point, the actual laser surgery procedure can begin and the patient is prepped at 328, as discussed above. The Pixmap spot (when step 326 is implemented) or entire Pixmap image (when step 327 is implemented) representing the initial location for ablation is then loaded at 330 into a buffer of the computer system 110. The eye tracking system 112 then calculates the movement of the eye and manipulates the buffered data such that the spot or image is translated accordingly. The Pixmap image is displayed at 334 on a video monitor 120 and the mirrors of the DMD are also arranged at 336 in an ON/OFF pattern to simulate the Pixmap image. The laser is then fired at 338 at the DMD mirror array.

When the laser 102 is fired at 338, it is shaped and conditioned by the optical system 104, and directed onto the mirror array of the DMD. The laser beam is then reflected at 340 by the mirror array. Each mirror reflects its associated portion of the laser pulse either away from or towards the cornea according to the respective ON/OFF positions of the mirrors. Additional optics then image at 342 the patterned laser beam onto the eye, preferably in demagnified ratio.

The procedure then continues at 330 for subsequent spot locations (where the system performs individual spot scanning emulation at 344) and/or for other layers of ablation (in both spot scanning mode and layer mode) until all layers have been treated in each optical zone requiring correction at 346. The resulting etch at 348 has per pixel resolution of the Pixmap image and is adapted to correct corneal topography defects. Depending upon the spot size, the procedure provides correction with a resolution at least as sharp as that of prior art systems. See, for example, scanning spot ablation patterns shown in FIGS. 8(*c*) and 8(*d*). With relatively smaller spots, greater resolution is achievable.

Corneal Topography Layer Approach

While a scanning spot system utilizing corneal topography provides superior results to broadbeam and traditional scanning spot approaches, any scanning spot approach is hindered in that its resolution is limited by the size of the scanned spot and the overlap of spots in a scanning spot approach. In response to this limitation, a corneal topography layer approach optimized for use with a DMD is now described.

Figure 1:
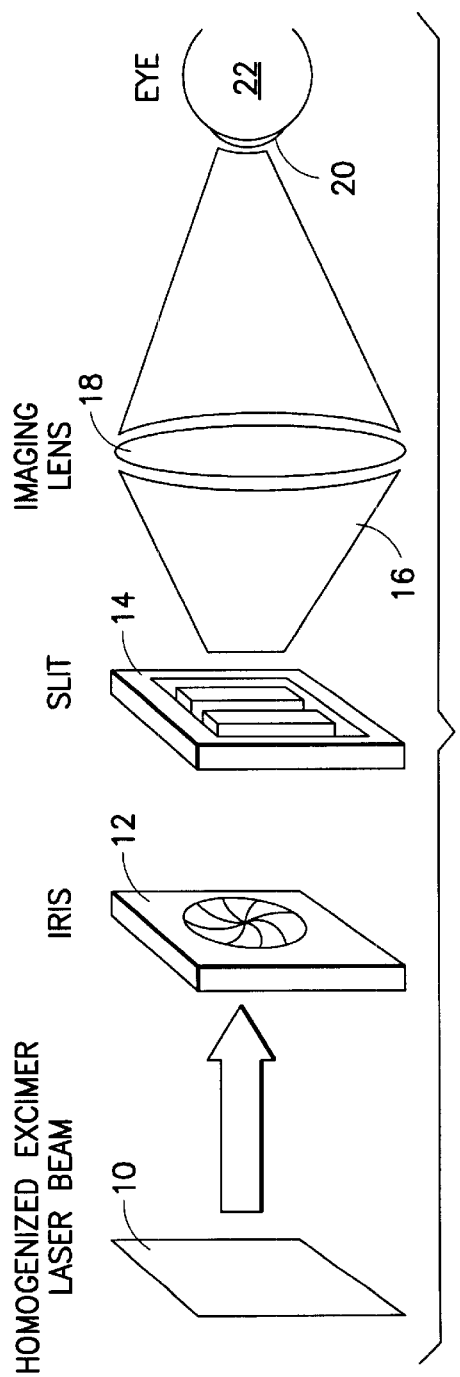
FIG. 1 is a schematic of a prior art broadbeam refractive laser system using an iris/slit approach.
Figure 2:
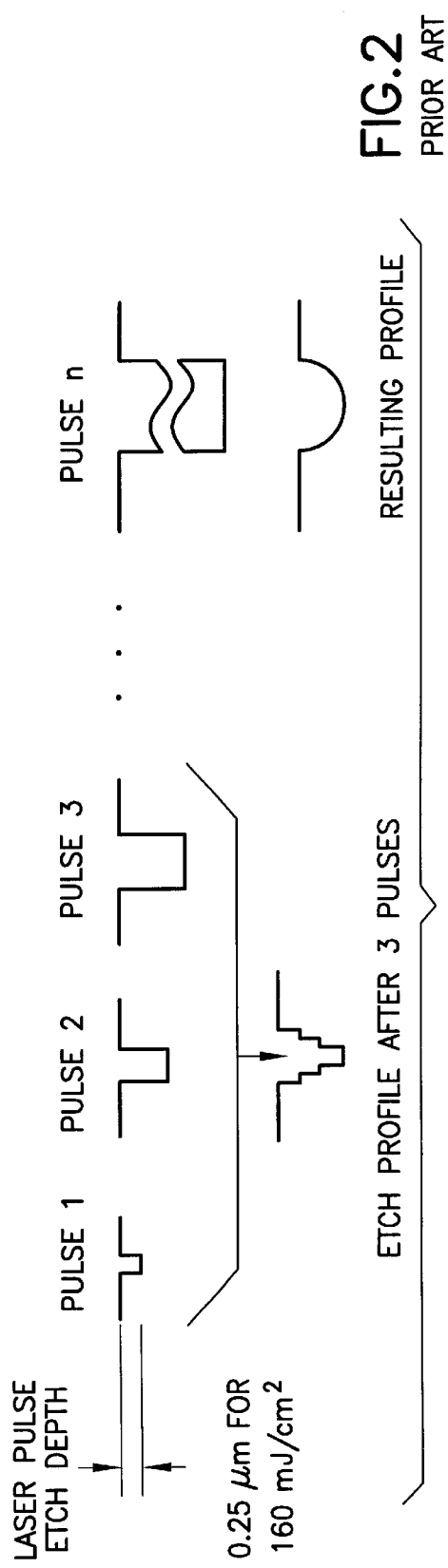
FIG. 2 is a schematic illustrating the prior art process of laser etching the cornea.
Figure 24:
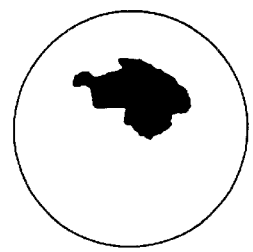
FIG. 24 illustrates the etch resolution provided by the procedure described in FIG. 23 with respect to the topography zone illustrated in FIG. 8b.
Figure 8D:
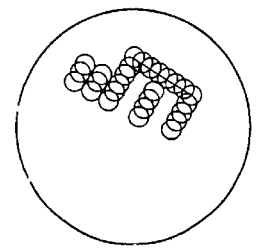
FIG. 8d illustrates a method of scanning a 0.5 mm diameter spot over the topography zone of FIG. 8b.
Figure 23A:
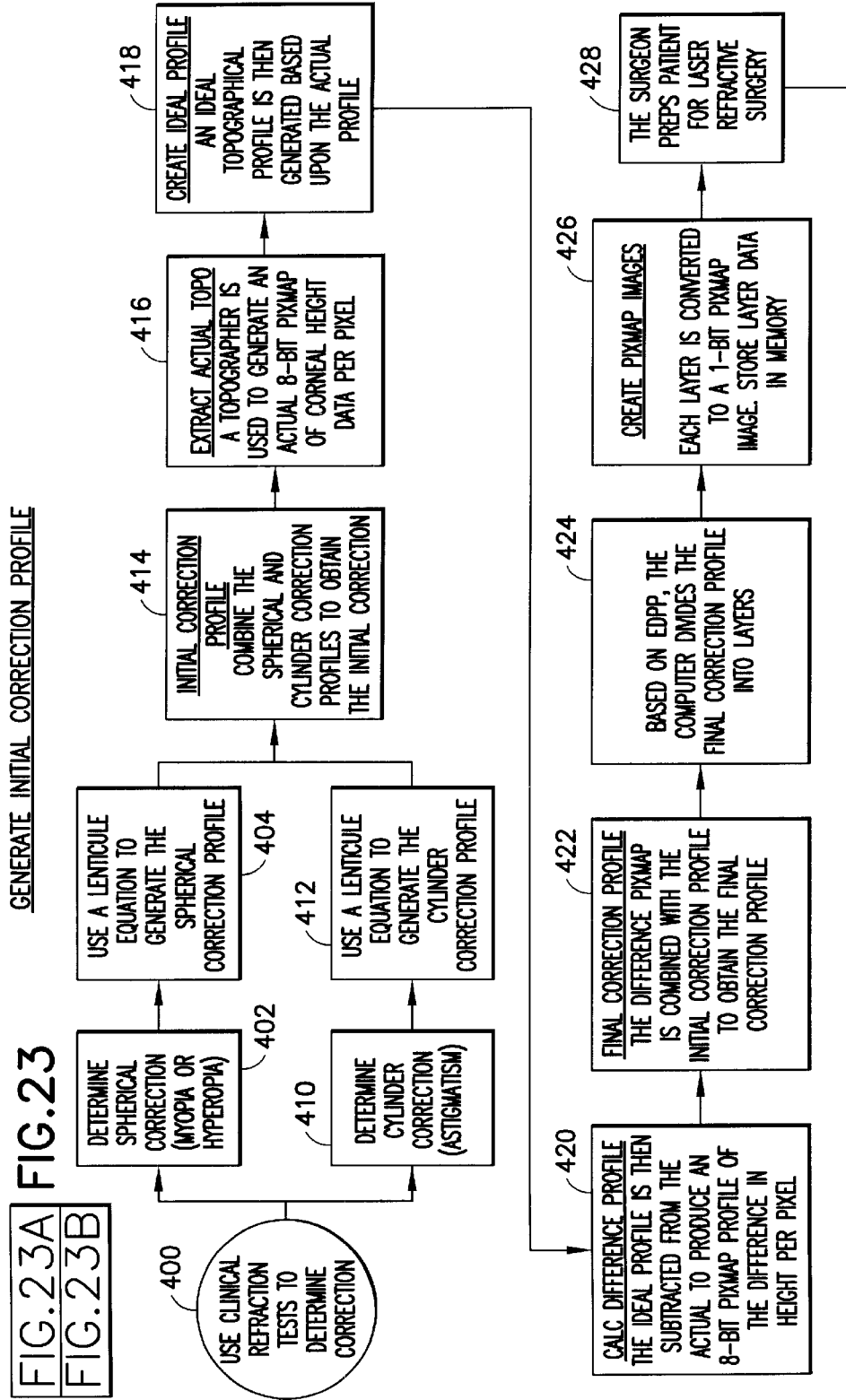
FIG. 23 is a flowchart for performing laser eye surgery in an approach utilizing corneal topography data and optimized for a DMD.
Figure 23B:
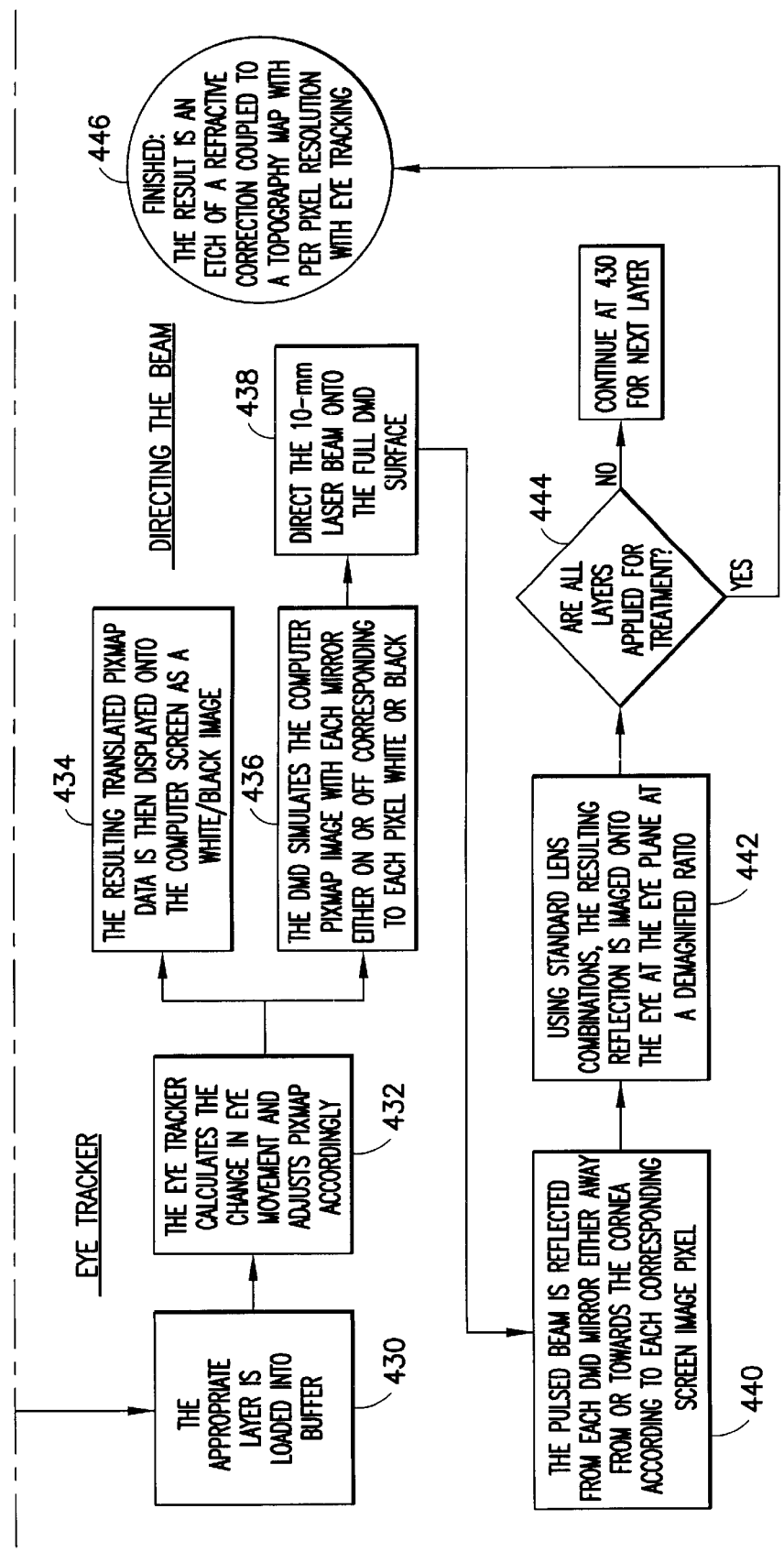

Referring to FIG. 23, the procedure is substantially similar to the above described spot scanning approach utilizing corneal topography data. As such, steps 400 to 422 correspond exactly to steps 300 to 322 in FIG. 22, which are described above. In accord with the present approach, after the final correction profile is obtained at 422, based on the etch depth per pulse (EDPP), the computer 110 divides the final correction profile into layers at 424. Each layer is converted at 426 into a 1 bit Pixmap image which is stored as data in a memory of the computer 110. At this point, the procedure continues and steps 428 to 442 correspond exactly to steps 328 to 342 in FIG. 22. After the laser beam is imaged at 442 onto the eye in the pattern of the Pixmap image for treatment of a particular correction layer, if at 444 there are additional layers requiring treatment, the procedure continues at 430. If at 444, no other layers require treatment, the procedure is completed at 446. As shown in FIG. 24, this approach (using 13 or 16 micron mirrors) can better match the corneal topography and other correction requirements than scanning spot systems (using a 0.5 mm or 1 mm spot). It is noted that this approach provides a resolution approximately 60 times the resolution of prior art scanning spot systems.

Wavefront Sensing Approach

By selecting the wavefront sensor mode of operation, the most advanced system for laser refraction is enabled. In order to select this mode, the laser surgery system 100 must be coupled to or adapted to receive data from a wavefront sensor system 140 (FIG. 9). The wavefront sensor system 140 analyzes the optical system of the eye 108 and provides data corresponding to a three dimensional representation of the optical system of the eye. The three dimensional results are translated into an array of optical wavefront data that characterizes the entire optical system of the eye. This information is preferably either in the form of topographical data (i.e., the height values that need to be corrected to arrive at an optimized corneal shape) or in optical power data (often referred to as K-readings). One such wavefront sensor system is disclosed in U.S. Pat. No. 5,777,719 to Williams, which utilizes a Hartmann-Shack sensor and which is hereby incorporated by reference herein in its entirety, and others are available or forthcoming from 20/10 Perfect Vision of Heidelberg, Germany; Technomed GmbH of Baesweiler, Germany; Bausch & Lomb Surgical of Claremont, Calif.; and Tracey Technologies of Bellaire, Tex.

Here, a visible laser beam, or a number of visible laser beams, are directed through the entire eye optical system: cornea, lens, vitreous and retina. The return reflection from the retina is recorded by a CCD camera and analyzed against an ideal wavefront. Thus, the entire optical system is analyzed. According to the invention, the result of this analysis, rather than providing data for creating an ideal topographical profile or initial correction profile (as is done in corneal topography driven systems), provides data which is directly used to control etching of the cornea.

Therefore, the laser refractive correction procedure will proceed much like that described above with respect to the corneal topography layer approach described above. The main difference is in the configuration of the wavefront analysis system: offline or real-time. In the offline approach a series of layers are generated before the surgery, stored and then used to guide the laser ablation to the cornea, as is done in the corneal topography layer approach. In the real-time approach the wavefront sensor is built into the refractive laser system and evaluates the cornea after every layer (or a sequence of layers) is ablated. This continues until feedback from the wavefront sensor indicates that the cornea has been modified to properly correct for aberration in the optical system of the eye.

Figure 8C:
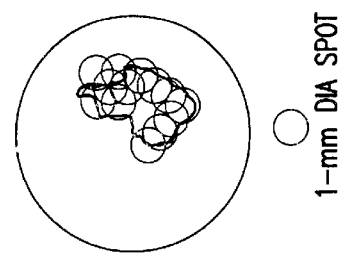
FIG. 8c illustrates a method of scanning a 1 mm diameter spot over the topography zone of FIG. 8b.
Figure 8B:
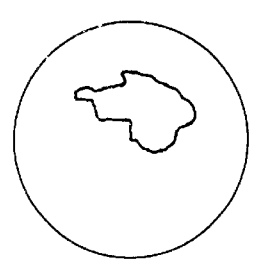
Figure 8A:
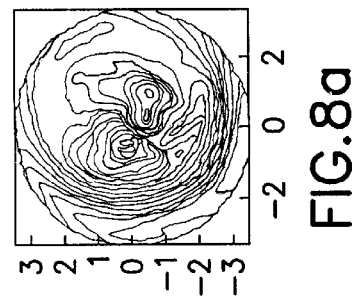
FIG. 8a is a three dimensional image defining several topography zones requiring ablation.
Figures 25, 25A:
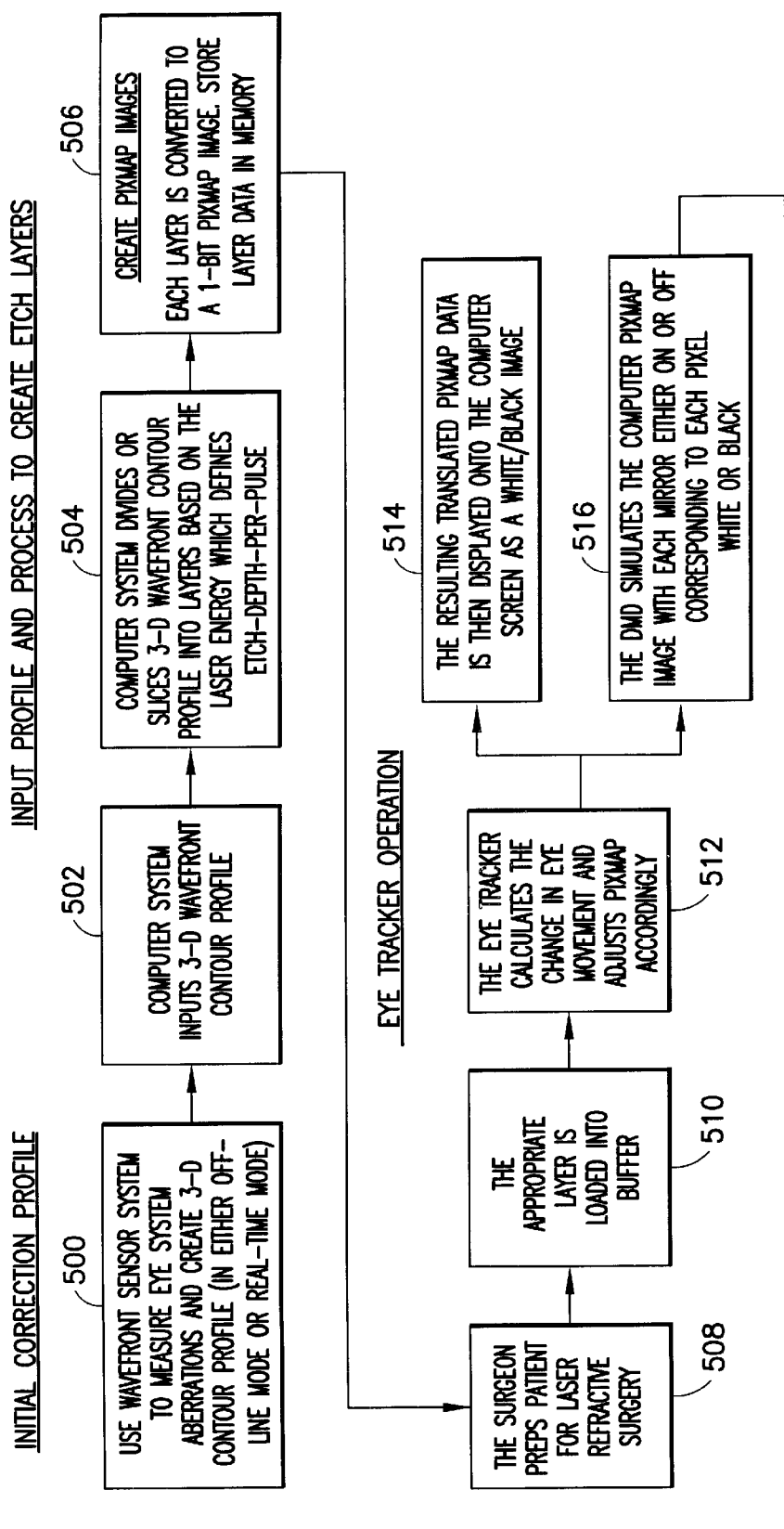
FIG. 25 is a flowchart for performing laser eye surgery in an approach utilizing wavefront sensor data and optimized for a DMD.
Figure 25B:
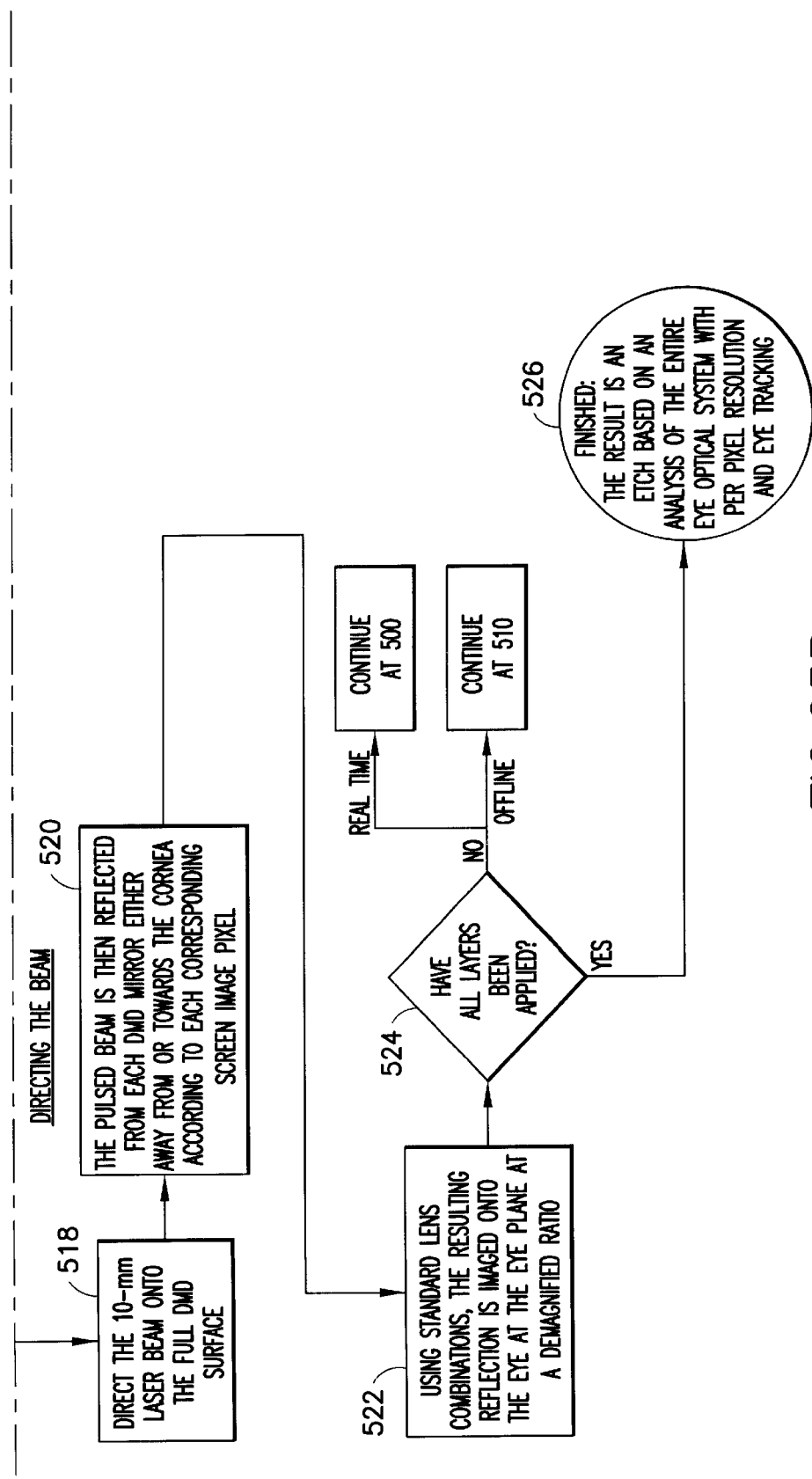

Referring to FIGS. 9 and 25, according to the wavefront sensor approach, in either the off-line or real-time approaches, the wavefront sensor system 140 measures the eye system aberrations and creates a 3-D contour profile (substantially similar to FIG. 8(a)) and data corresponding thereto is input at 502 into the computer system 110. The computer system then divides or slices at 504 the contour profile (3-D data) into layers (a series of 2-D data points) based on the EDPP. Each layer is converted at 506 into a 1-bit Pixmap image and stored as layer data in a memory of the computer system 110. The surgeon then preps at 508 the patient for laser refractive surgery (PRK or LASIK). The appropriate layer data is then loaded at 510 into a buffer. The eye tracker calculates movement of the eye and adjusts or translates at 512 the Pixmap image accordingly. The translated Pixmap image is displayed at 514 on the video monitor 120, and also provided at 516 to the DMD 106 through the DMD controller 118 such that the DMD simulates the Pixmap image. The laser beam is directed at 518 to the DMD mirror array surface and then reflected at 520 by the DMD surface toward the cornea in accord with the Pixmap image. Optics image at 522 the reflection onto the eye, preferably at a demagnified ratio. In real-time mode, the procedure repeats at 500, with a subsequent wavefront sensor analysis of the eye system. The process is repeated until the wavefront sensor analysis confirms that the eye system has been corrected within a preferred margin of error. In off-line mode, the procedure continues at 510 with the loading of the next layer for correction. In either mode, at 526, once all layers have been etched the entire optical system of the eye is corrected with per pixel resolution.

Each of the offline and real-time approaches are disclosed in more detail in previously incorporated parent application U.S. Ser. No. 09/524,312.

In view of the above, a laser surgery system is provided which is adaptable to emulate and/or perform every currently used approach to laser surgery. That is, as the techniques are controlled by software coupled to a DMD and not limited by hardware requirements, a single laser surgery system may be used to operate according to any of the above described approaches. Moreover, unlike any prior art system, the laser surgery system can directly match corneal topography or wavefront sensor data "point-to-point" from data points to individual DMD mirrors. That is, since corneal topography and wavefront sensor systems are both digital in nature and offer 2-D digital information, the digital information may be directly mapped to the 2-D array of mirrors of the DMD. Furthermore, the laser surgery system is capable of providing significantly greater resolution than prior art systems as the individual mirrors of the DMD are 13 or 16 microns in size. As DMDs become available with greater numbers of mirrors of smaller size, the resolution of the techniques described herein will likewise be increased.

There have been described and illustrated an embodiment of a laser surgery system and methods of using the same. While particular embodiments of the invention have been described, it is not intended that the invention be limited thereto, as it is intended that the invention be as broad in scope as the art will allow and that the specification be read likewise. Thus, while particular prior art systems have been described for emulation, it will be appreciated that other systems may be emulated as well. In addition, while particular types of scanning methods have been disclosed, it will be appreciated that other scanning methods can be used as well. Also, while a laser surgery system which can emulate all of the broadbeam, corneal topography scanning spot, and wavefront sensor scanning spot techniques has been described, it will be appreciated that a laser surgery system which emulates only at least one of the techniques can be provided, as such will include the advantage of the superior resolution provided by the DMD. As such, while it is preferable that a corneal topographer or a wavefront sensor system be included in the laser surgery system, neither is required. In addition, while the invention is described with respect to a variation of Munnerlyn's equation, the unvaried Munnerlyn's equation (both collectively referred to as Munnerlyn's equation in the claims) or any other lenticule equation, e.g., Schwiegerling's higher order equation, may be used. Moreover, while a number of scanning methods with differing overlaps have been disclosed, it will be appreciated that no overlap is required in any scanning spot emulation, due to the relatively high resolution of the DMD and the ability to slightly defocus at the cornea. Furthermore, while particular orders of steps for the methods (as shown in the flowcharts) are preferred, it will be appreciated that the steps can be performed in another order. It will therefore be appreciated by those skilled in the art that yet other modifications could be made to the provided invention without deviating from its spirit and scope as claimed.

What is claimed is:

1. A method of directing mirrors of a digital micromirror device (DMD) used in a laser eye surgery system having a computer, comprising:
   a) inputting eye refraction data into the computer;
   b) generating with the computer spherical and cylinder refraction correction profiles from said eye refraction data;
   c) creating a sequence of layer image data for at least one of a spherical and a cylinder correction profile;
   d) transferring said sequence of layer image data to the DMD; and
   e) directing a broadbeam laser to the DMD.

2. A method according to claim 1, wherein:
   for each of said spherical and said cylinder correction profiles, said layer image data is created, and said layer image data is combined.

3. A method according to claim 1, wherein:

said layer image data is divided into spot-sized portions.

4. A method according to claim 1, wherein:

said inputting eye refraction data includes inputting corneal topography data into the computer, said method further comprising, f) modifying said at least one of said spherical and cylinder refraction correction profiles relative to said corneal topography data, wherein said sequence of layer image data is created for said modified refraction correction profile.

5. A method according to claim 4, wherein:

said layer image data includes corneal height information.

6. A method according to claim 5, wherein:

said layer image data is divided into a series of 1 bit images.

7. A method according to claim 6, wherein:

each 1 bit image corresponds to an etch depth of a pulse of said laser.

8. A laser surgery system for reshaping the cornea of the eye, said system comprising:

a) means for generating a spherical correction profile and a cylinder correction profile;

b) means for determining iris size data for each of a plurality of slices through said spherical correction profile and slit size data for each of a plurality of slices through said cylinder correction profile;

c) means for merging said iris size data and said slit size data for each said respective plurality of slices into a data array;

d) means for creating a plurality of one-bit resolution images from said data array;

e) a digital micromirror device (DMD) having a plurality of mirrors and adapted to modulate said mirrors into patterns corresponding to said one-bit resolution images; and f) a laser adapted to direct a broadbeam laser beam at said DMD such that a laser beam produced by said laser is shaped into said patterns and redirected by said DMD to the eye.

9. A laser surgery system according to claim 8, wherein:

each of said one-bit resolution images corresponds to a particular etch depth in the cornea.

* * * * *

UNITED STATES PATENT AND TRADEMARK OFFICE
CERTIFICATE OF CORRECTION

PATENT NO.     : 6,413,251 B1
DATED          : July 2, 2002
INVENTOR(S)    : Roy E. Williams It is certified that error appears in the above-identified patent and that said Letters Patent is hereby corrected as shown below:

<u>Title page, Item [54] and Column 1, line 2,</u>
Title, "MIRCOMIRROR" should be -- MICROMIRROR --

Signed and Sealed this

Sixth Day of August, 2002

Attest:

Attesting Officer

JAMES E. ROGAN
*Director of the United States Patent and Trademark Office*